(12) United States Patent
Holtman et al.

(10) Patent No.: US 8,710,069 B2
(45) Date of Patent: Apr. 29, 2014

(54) OPIOID-NORNICOTINE CODRUGS COMBINATIONS FOR PAIN MANAGEMENT

(75) Inventors: Joseph R. Holtman, Lexington, KY (US); Peter A. Crooks, Nicholasville, KY (US); Ujjwal Chakraborty, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 581 days.

(21) Appl. No.: 12/934,861

(22) PCT Filed: Mar. 27, 2009

(86) PCT No.: PCT/US2009/038664
§ 371 (c)(1),
(2), (4) Date: Nov. 30, 2010

(87) PCT Pub. No.: WO2009/121018
PCT Pub. Date: Oct. 1, 2009

(65) Prior Publication Data
US 2011/0112130 A1    May 12, 2011

Related U.S. Application Data

(60) Provisional application No. 61/072,091, filed on Mar. 27, 2008.

(51) Int. Cl.
*A61K 31/44* (2006.01)
*A61K 31/35* (2006.01)
*C07D 405/00* (2006.01)
*C07D 221/22* (2006.01)

(52) U.S. Cl.
USPC .............. 514/282; 514/454; 546/207; 546/44

(58) Field of Classification Search
USPC ...................... 546/207, 282, 44; 514/282, 454
See application file for complete search history.

(56) References Cited

U.S. PATENT DOCUMENTS

| | | | |
|---|---|---|---|
| 5,149,704 A | 9/1992 | Summers et al. | |
| 5,460,826 A | 10/1995 | Merrill et al. | |
| 6,281,376 B1 | 8/2001 | Whittaker et al. | |
| 6,713,470 B2 * | 3/2004 | Jackson | 514/211.05 |
| 6,855,807 B1 * | 2/2005 | Devi et al. | 530/350 |
| 2005/0281845 A1 | 12/2005 | Bachmann et al. | |
| 2007/0123468 A1 | 5/2007 | Jenkins et al. | |

OTHER PUBLICATIONS

International Search Report dated Sep. 9, 2009 (One (1) page).

* cited by examiner

*Primary Examiner* — Andrew D Kosar
*Assistant Examiner* — Raymond Covington
(74) *Attorney, Agent, or Firm* — Crowell & Moring LLP

(57) ABSTRACT

The present invention relates to the field of pain management, and more particularly to synergistic codrugs comprising an opioid and nornicotine which have been combined to form a single chemical codrug entity. When the codrug is administered it produces a synergistic analgesic response to pain.

34 Claims, 19 Drawing Sheets

OPIOID-NORNICOTINE CODRUGS COMBINATIONS FOR PAIN MANAGEMENT

This application claims priority from U.S. Provisional Patent Application No. 61/072,091, filed Mar. 27, 2008, the disclosure of which is hereby incorporated by reference in its entirety.

FIELD OF THE INVENTION

The present invention relates to the field of pain management, and more particularly to synergistic codrugs comprising an opioid and nornicotine which have been combined to form a single chemical codrug entity. When the codrug is administered it produces a synergistic analgesic response to pain.

BACKGROUND OF INVENTION

Opioids are any endogenous or exogenous compounds that bind to an opioid receptor. Opioid receptors are localized primarily in the brain, spinal cord, and gastrointestinal tract. When opioids bind to their receptors in the brain and spinal cord they block pain transmission signals from the periphery of the body. Although opioids are very effective for moderate to severe pain, there are many well known problems associated with opioid therapy. Those problems include serious side effects such as cognitive dysfunction, respiratory depression, nausea/vomiting, urinary retention, and constipation. Further, chronic opioid therapy often results in the development of tolerance to the analgesic effect, resulting in dose escalation, as well as physical and psychological dependence.

Nornicotine, the primary metabolite of nicotine, binds to nicotinic receptors which are located in the brain, spinal cord and periphery (autonomic ganglia and smooth muscle). It has recently been appreciated that nicotinic receptor binding can also modulate pain signals to the brain suggesting their potential use in the treatment of pain (acute, chronic, cancer-related).

There is a great need for analgesic medications able to provide high efficacy pain relief while providing more favorable pharmacokinetics and reducing the possibility of undesirable effects. Enhancement of the analgesic effect of opioids as well as nornicotine has been described in the art Therefore, there is a need for a way to administer opioids and nornicotine to provide a more favorable pharmacokinetic profile.

SUMMARY OF THE INVENTION

The present invention provides a codrug of the following formula:

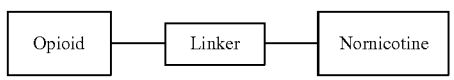

as well as pharmaceutical compositions thereof. The linker may be

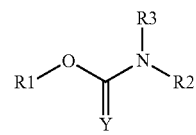

wherein Y is O or S; R1 is an opioid moiety; and R2-N—R3 is a nornicotine moiety; or

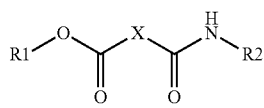

wherein X is nothing, O, S, NH, NR4 (where R4=alkyl), $(CH_2)_x$ (where x=1-20, and alkyl is linear or branched), and wherein R1-O is an opioid moiety and R2-N—R3 is a nornicotine moiety.

In another embodiment, the present invention provides a method of of synthesis of a codrug comprising a linker, an opioid and a nornicotine, said method comprising: a) covalently bonding a first attachment point of the linker to the opioid; b) covalently bonding a second attachment point of the linker to the nornicotine; and c) recovering the codrug, wherein the nornicotine is selected from the group consisting of S-nornicotine, R-nornicotine, and racemic nornicotine.

In another embodiment, the present invention provides a method of treatment comprising: joining an opioid together with a nornicotine using a linker to form a cleavable codrug; and administering an analgesically effective amount of the codrug to a human patient, wherein the nornicotine is selected from the group consisting of S-nornicotine, R-nornicotine, and racemic nornicotine.

DETAILED DESCRIPTION

Figure 1:
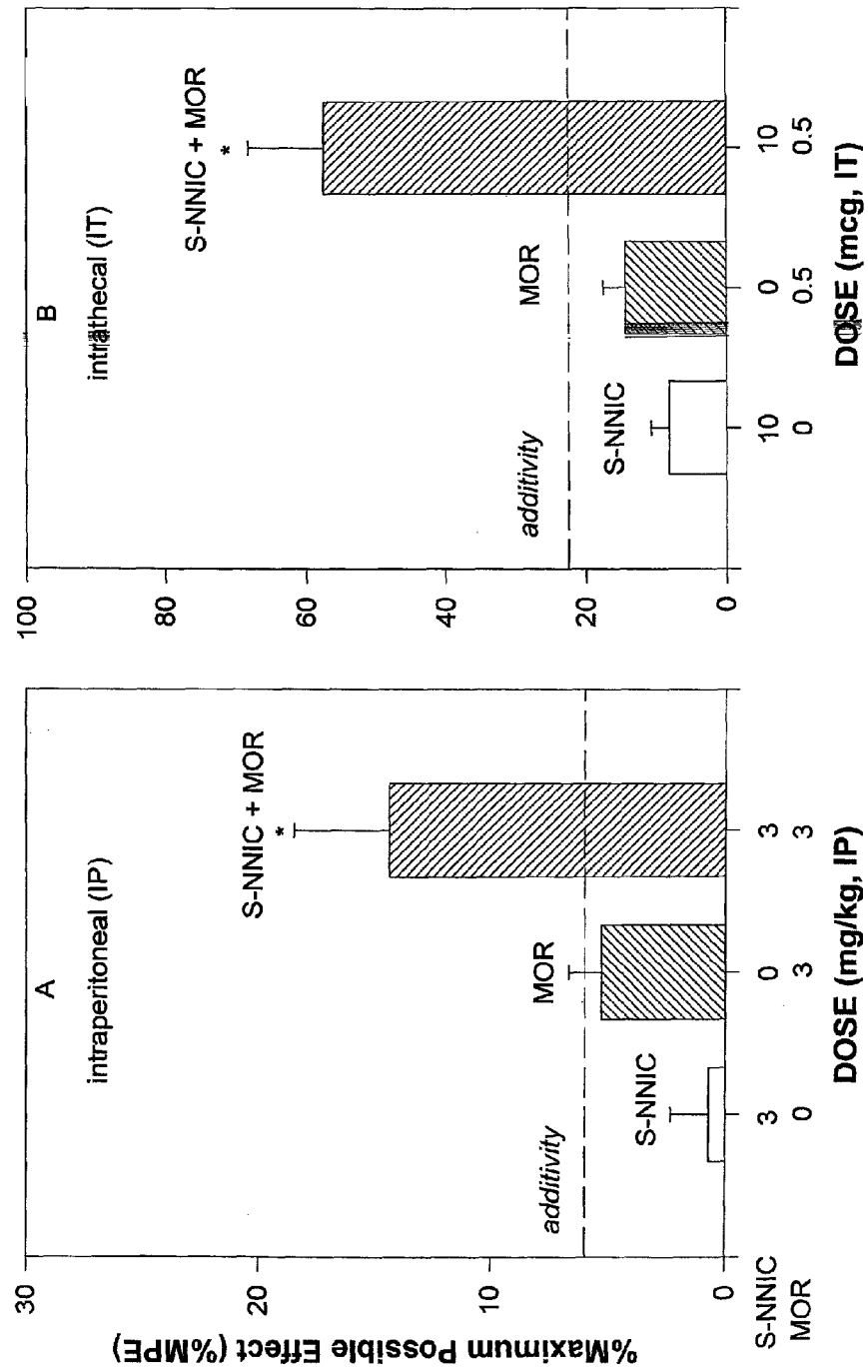
FIG. 1 is a graph illustrating the effect of S-nornicotine (S-NNIC) and morphine (MOR) combinations thermal antinociception, using the tail flick test.
Figure 2:
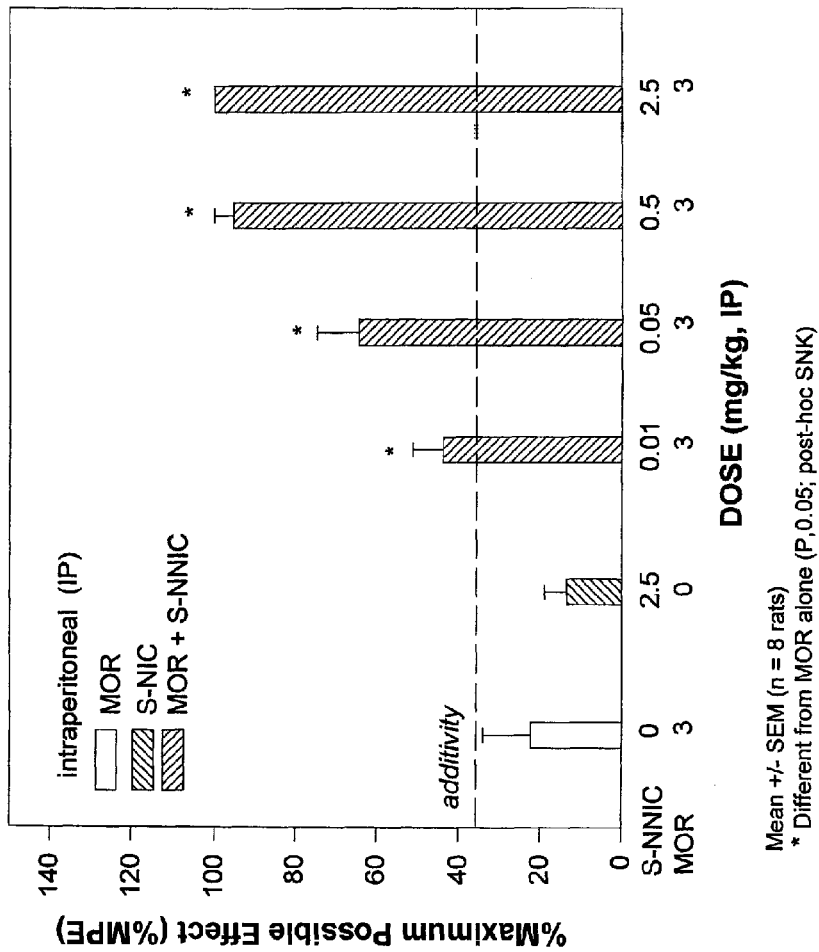
FIG. 2 is a graph illustrating the effect of S-nornicotine (S-NNIC) and morphine (MOR) combinations mechanical hyperalgesia.
Figure 3:
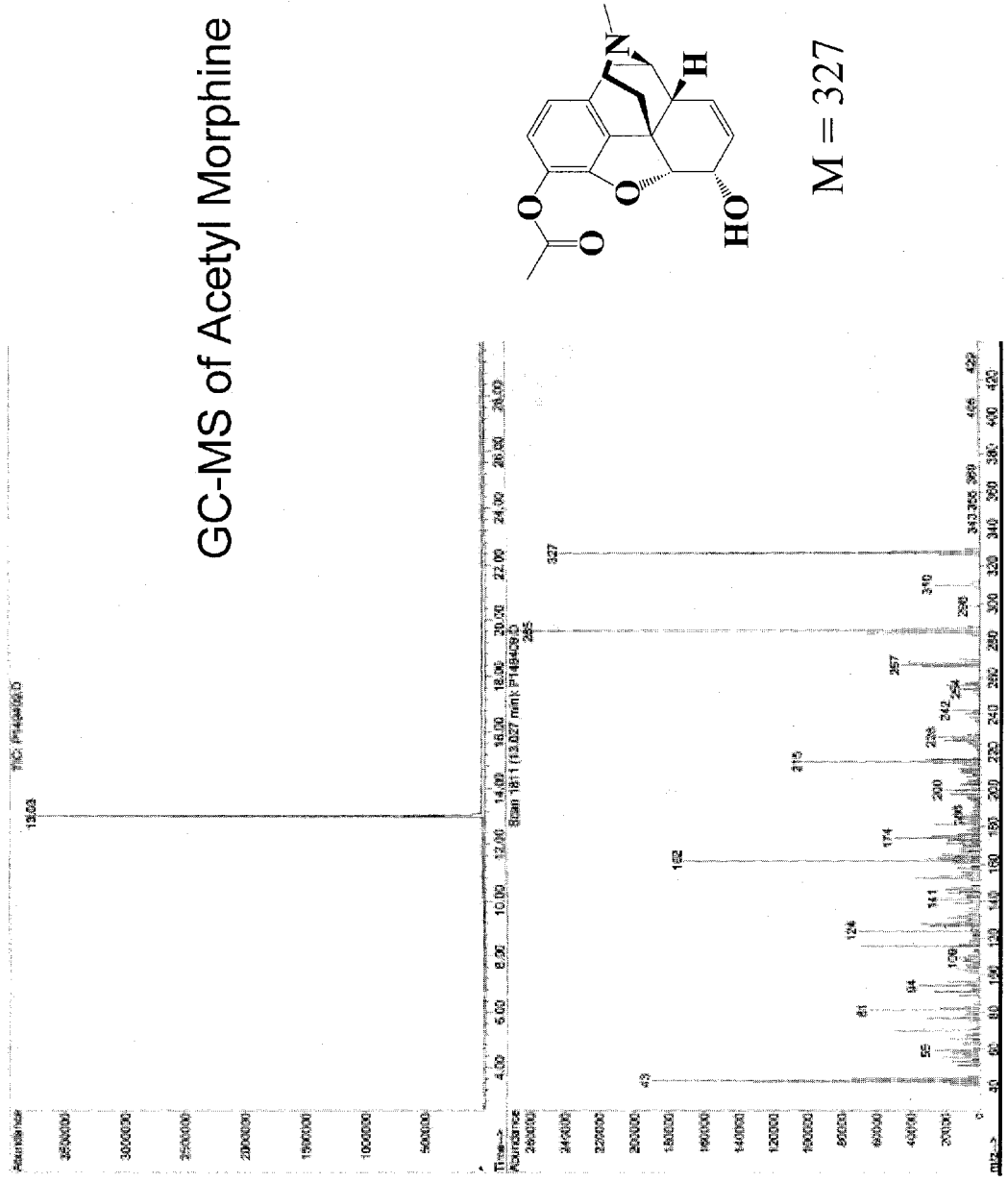
FIG. 3 shows codrug of 3-acetylmorphine and S-nornicotine of GC-MS of acetyl morphine.
Figure 4:
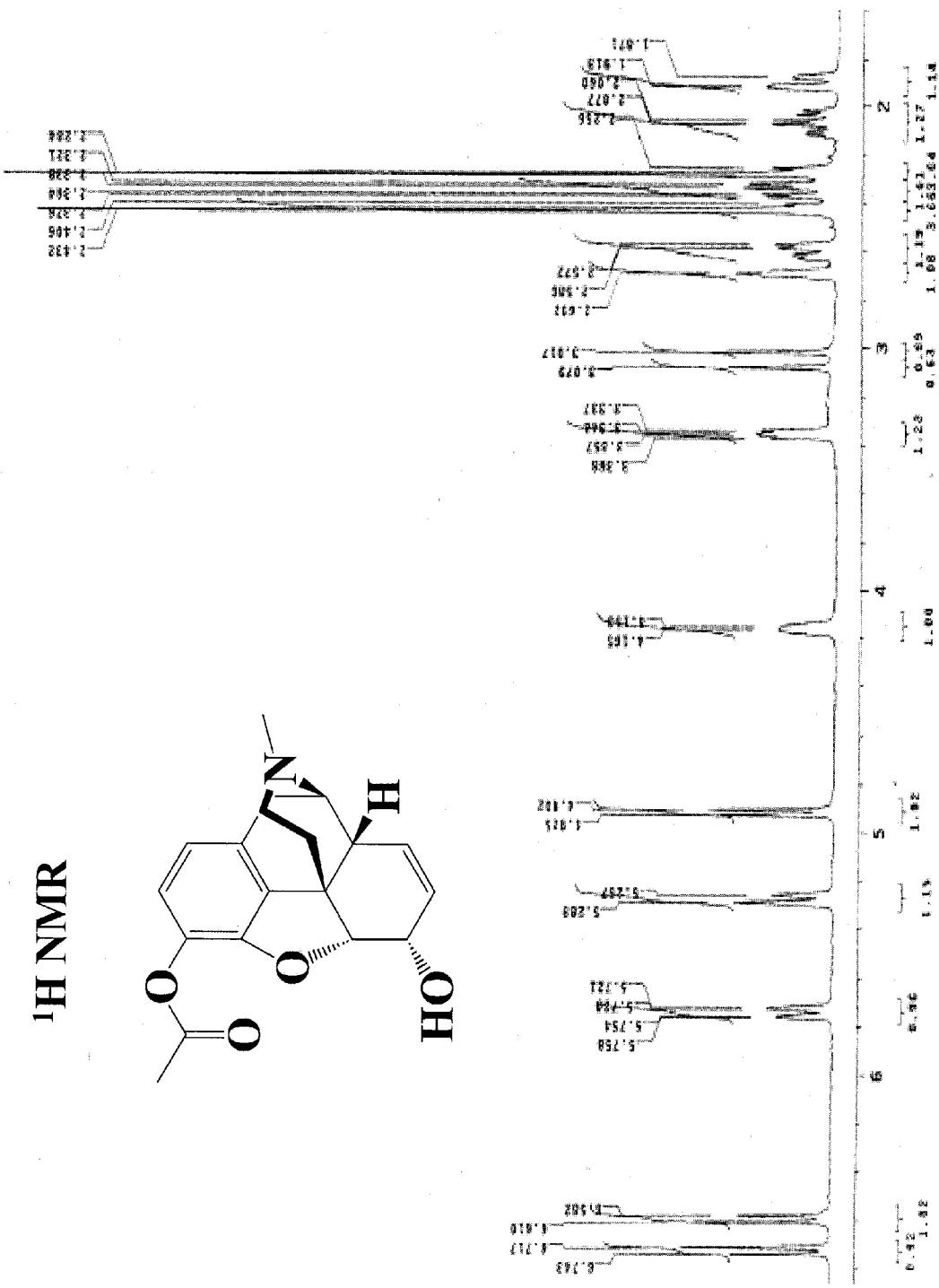
FIG. 4 shows H-NMR analysis of acetyl morphine.
Figure 5:
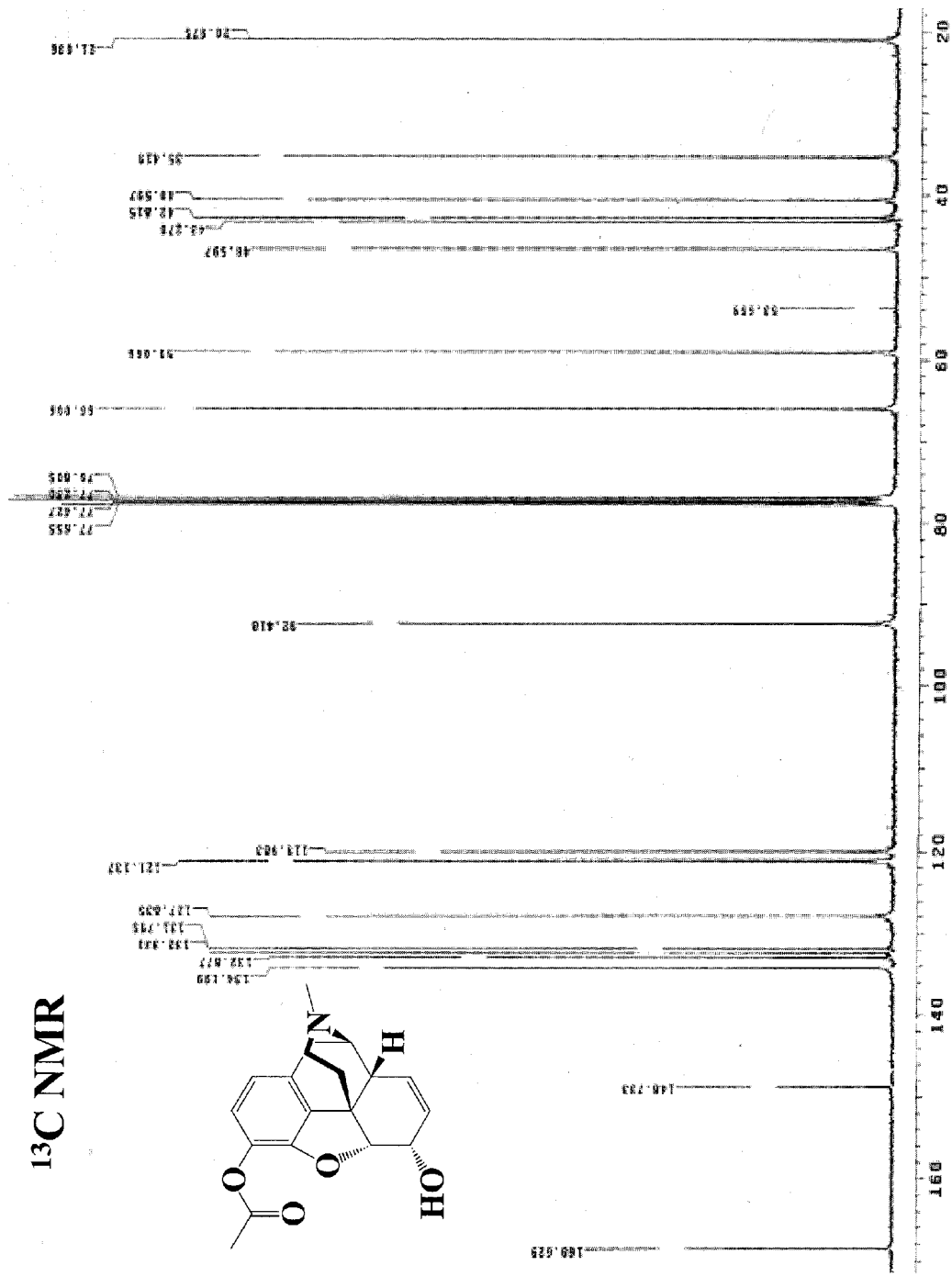
FIG. 5 shows C-NMR of acetyl morphine.
Figure 6:
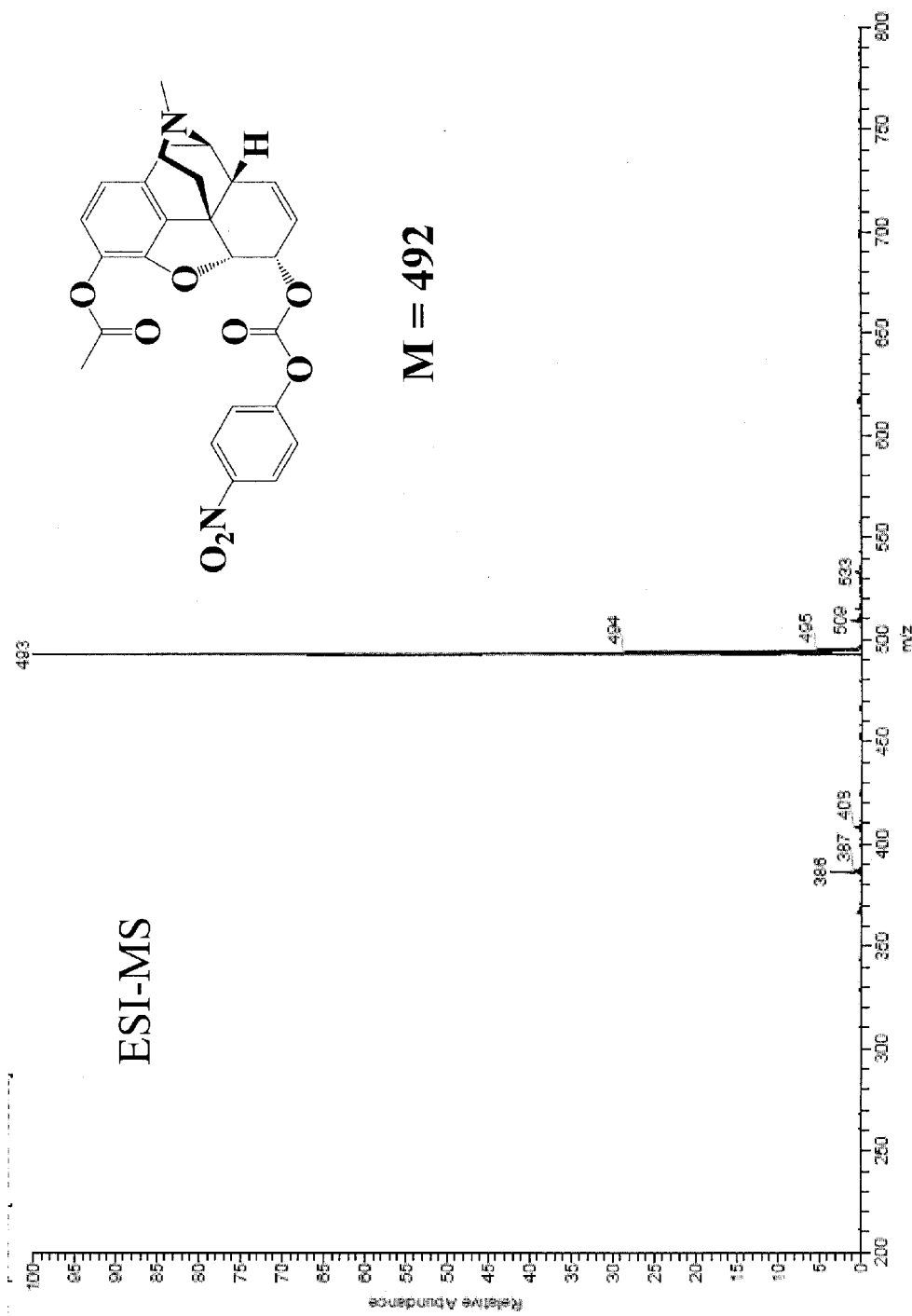
FIG. 6 shows ESI-MS of the para-nitrophenoxycarbamate ester of codeine.
Figure 7:
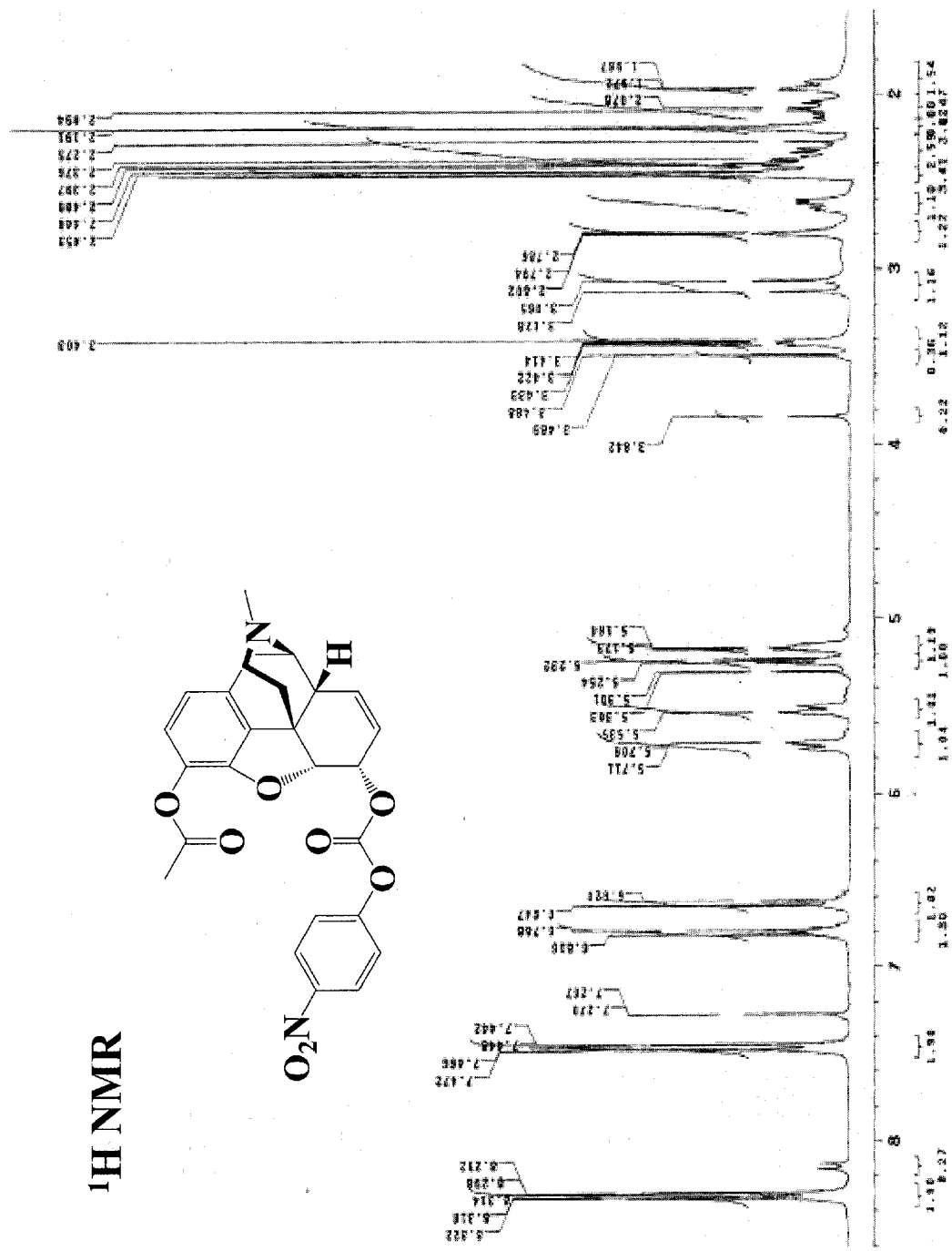
FIG. 7 shows H-NMR analysis of the para-nitrophenoxycarbamate ester of codeine.
Figure 8:
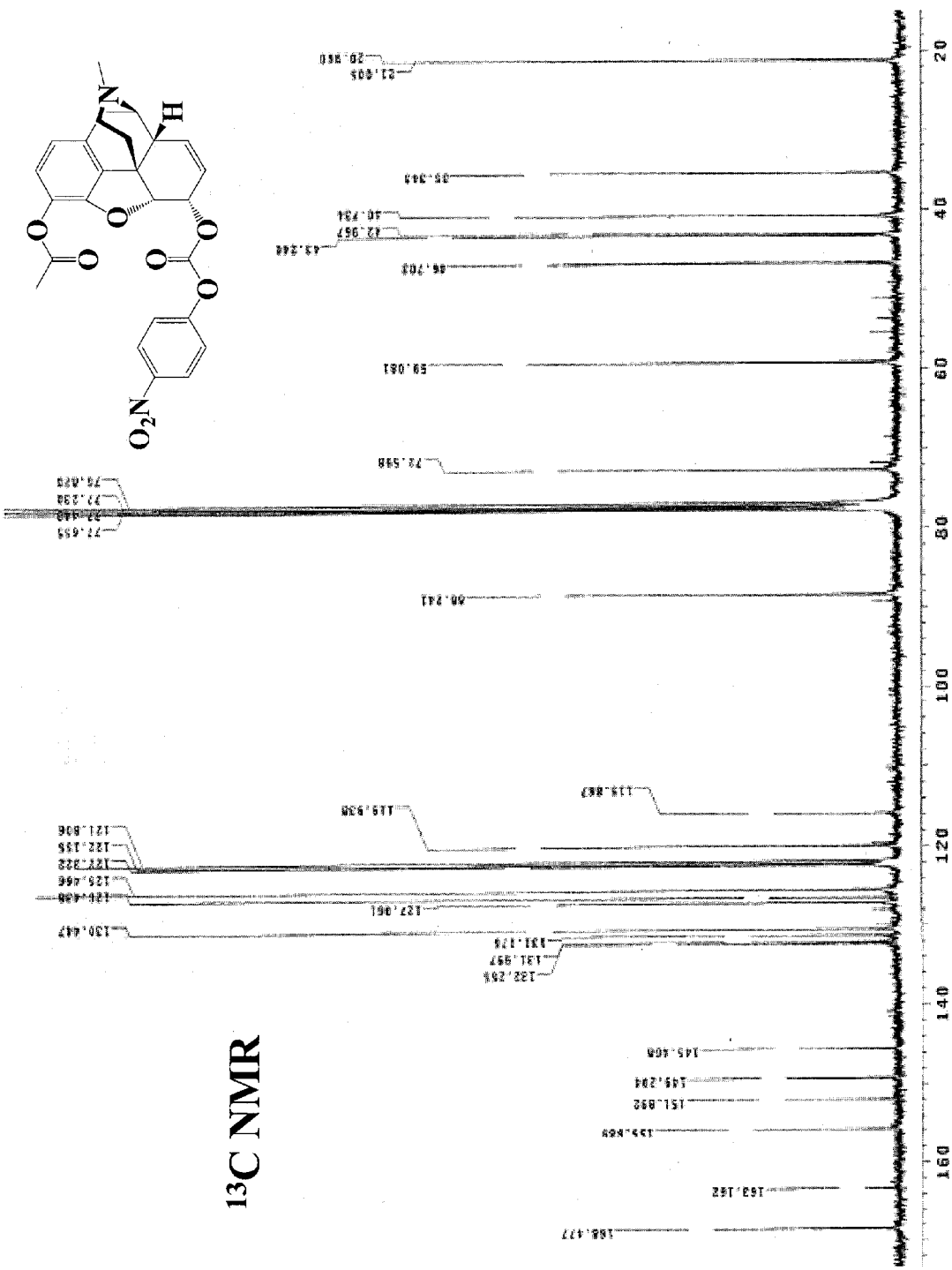
FIG. 8 shows C-NMR of the para-nitrophenoxycarbamate ester of codeine.
Figure 9:
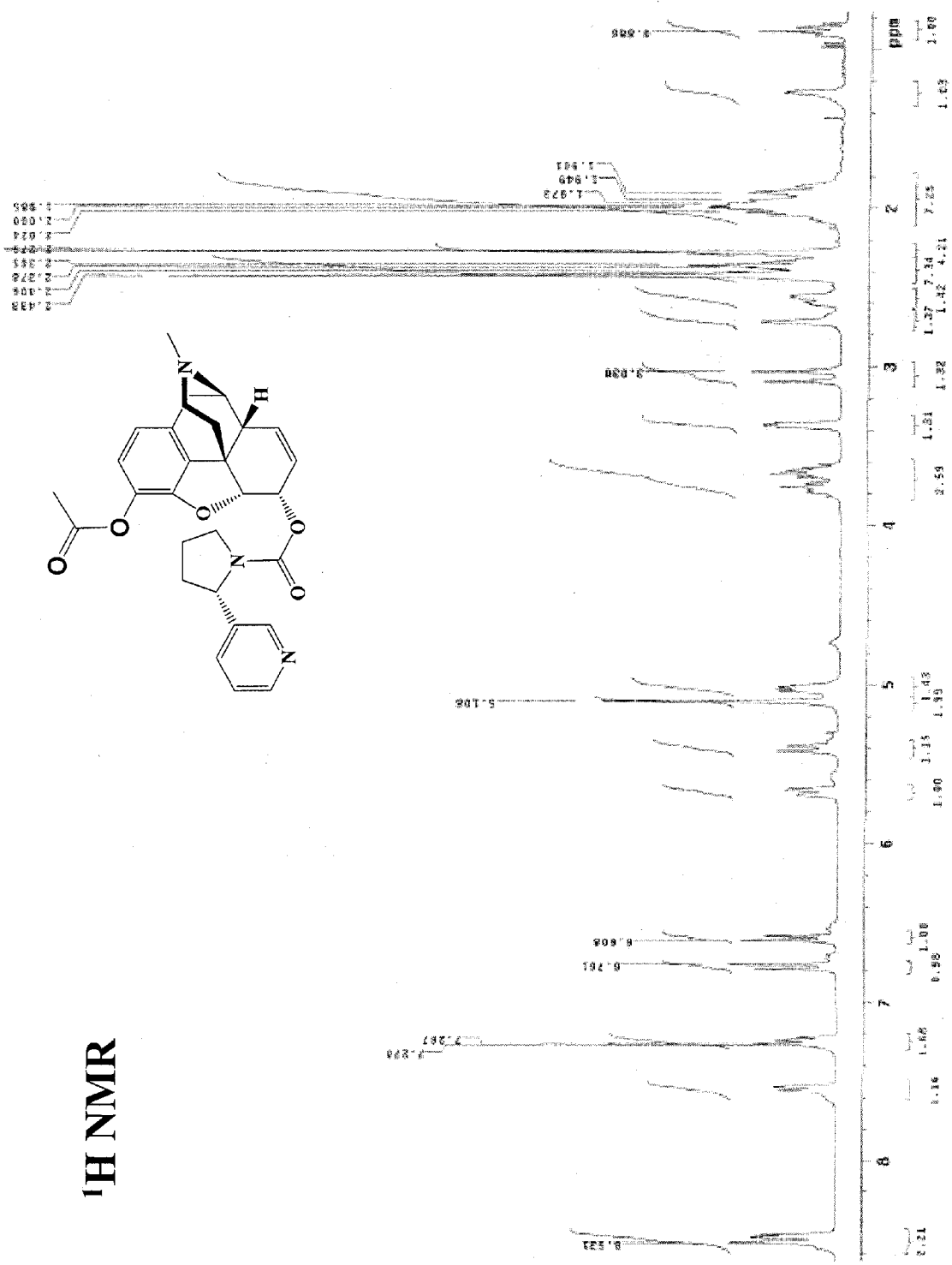
FIG. 9 shows H-NMR of an acetyl morphine and S-nornicotine codrug.
Figure 10:
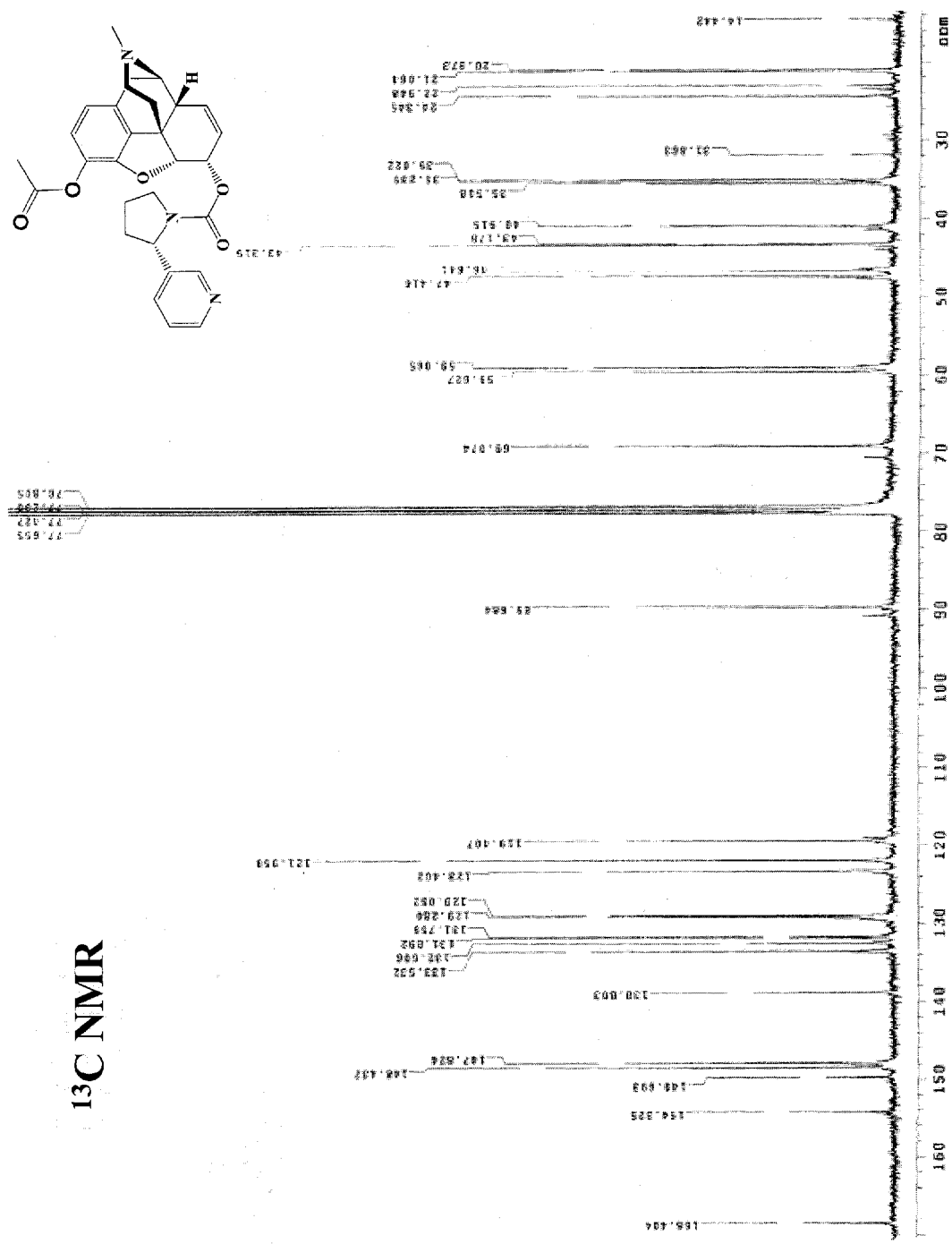
FIG. 10 shows C-NMR of an acetyl morphine and S-nornicotine codrug.
Figure 11:
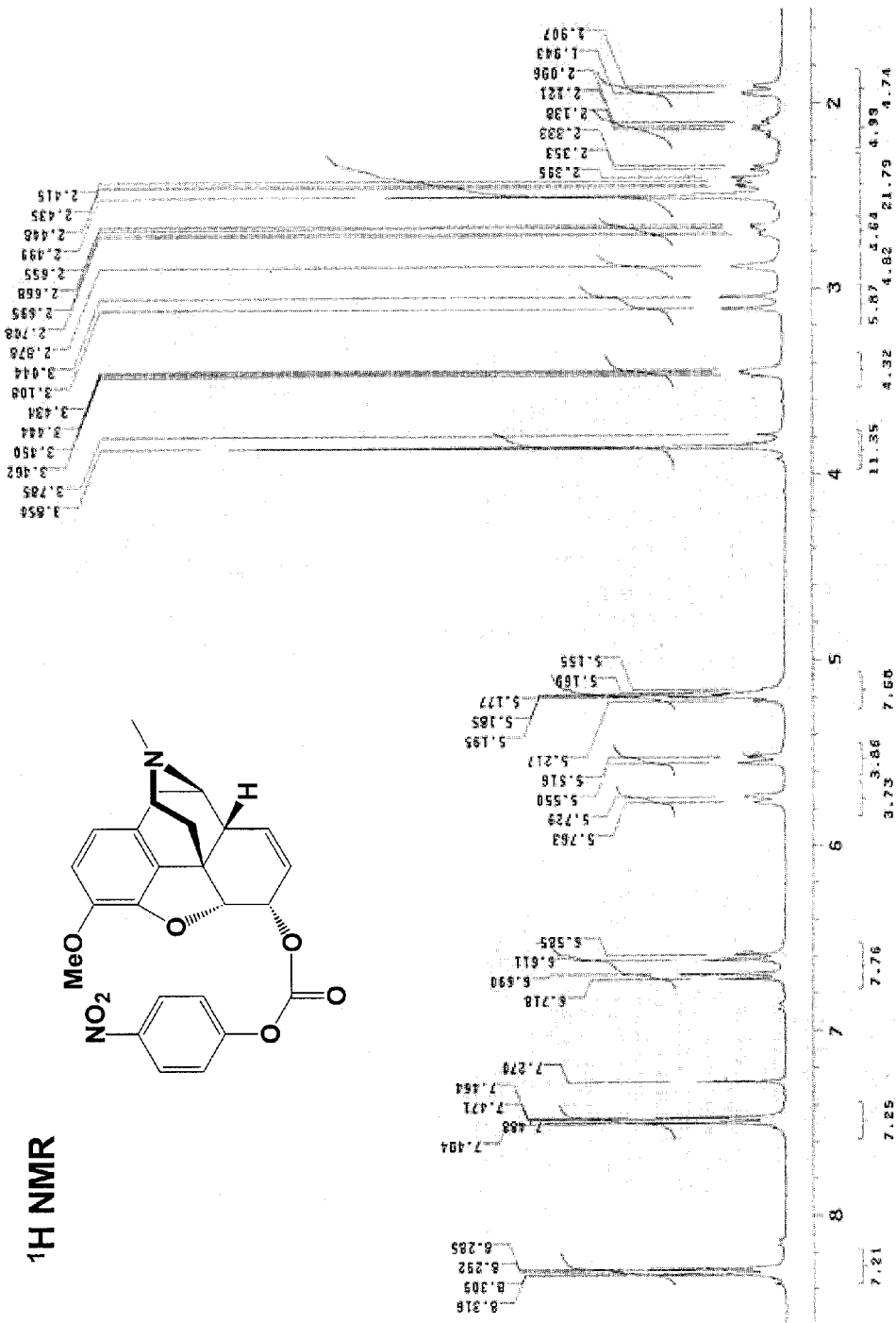
FIG. 11 shows H-NMR analysis of an intermediate in the preparation of a codrug of codeine and S-nornicotine.
Figure 12:
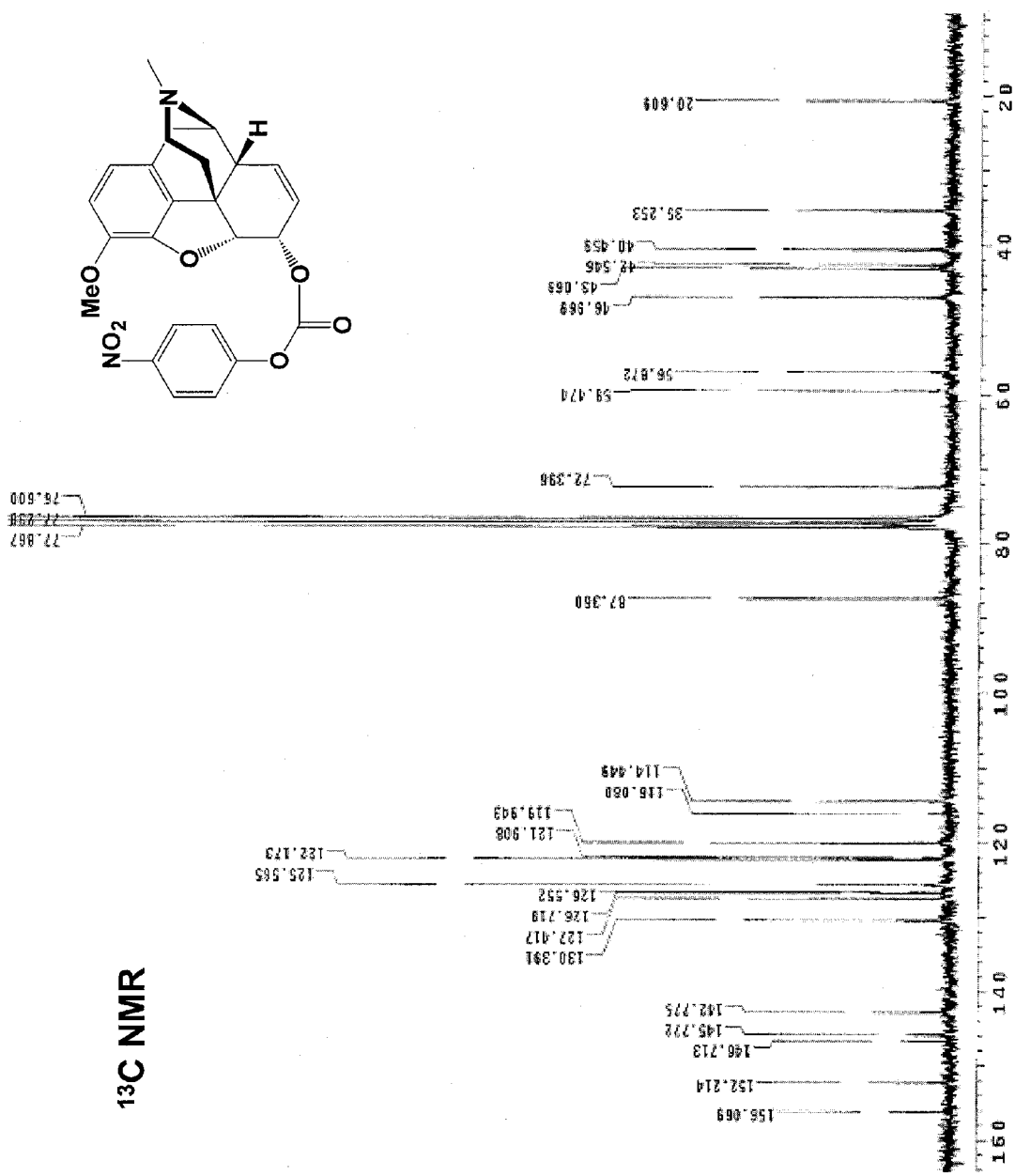
FIG. 12 shows C-NMR analysis of an intermediate in the preparation of a codrug of codeine and S-nornicotine.
Figure 13:
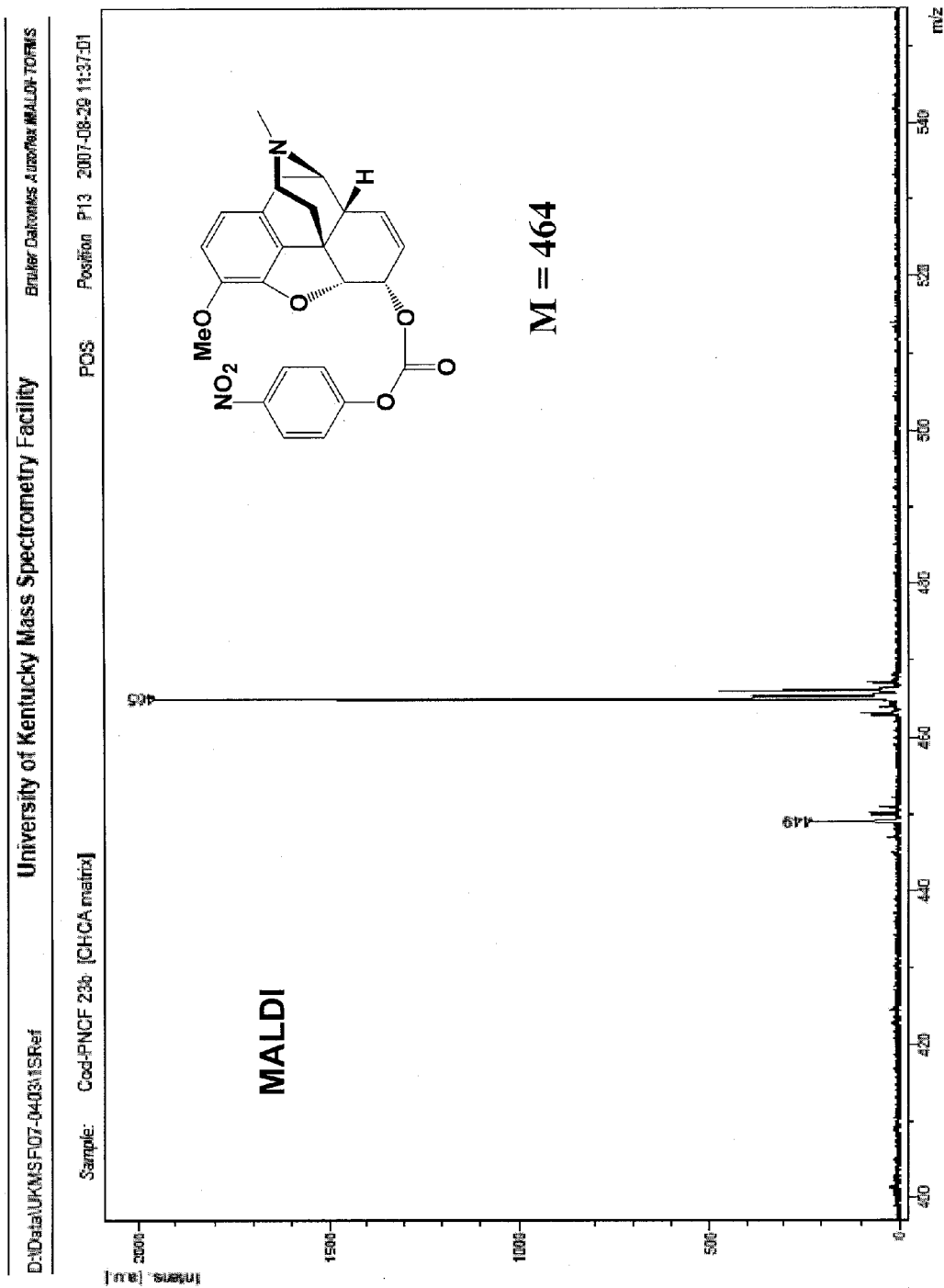
FIG. 13 shows MALDI analysis of an intermediate in the preparation of a codrug of codeine and S-nornicotine.
Figure 14:
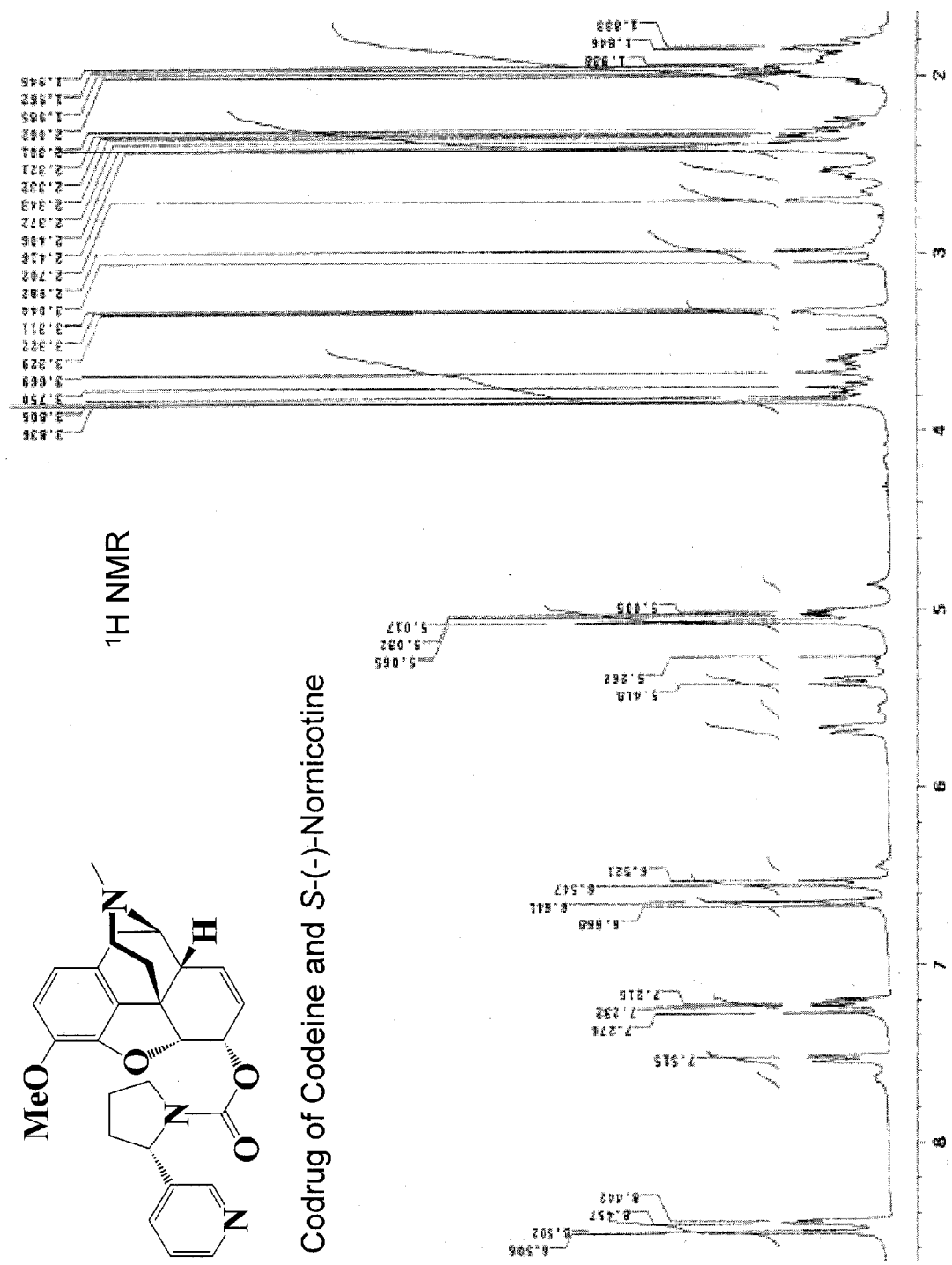
FIG. 14 shows H-NMR analysis of a codrug of codeine and S-nornicotine.
Figure 15:
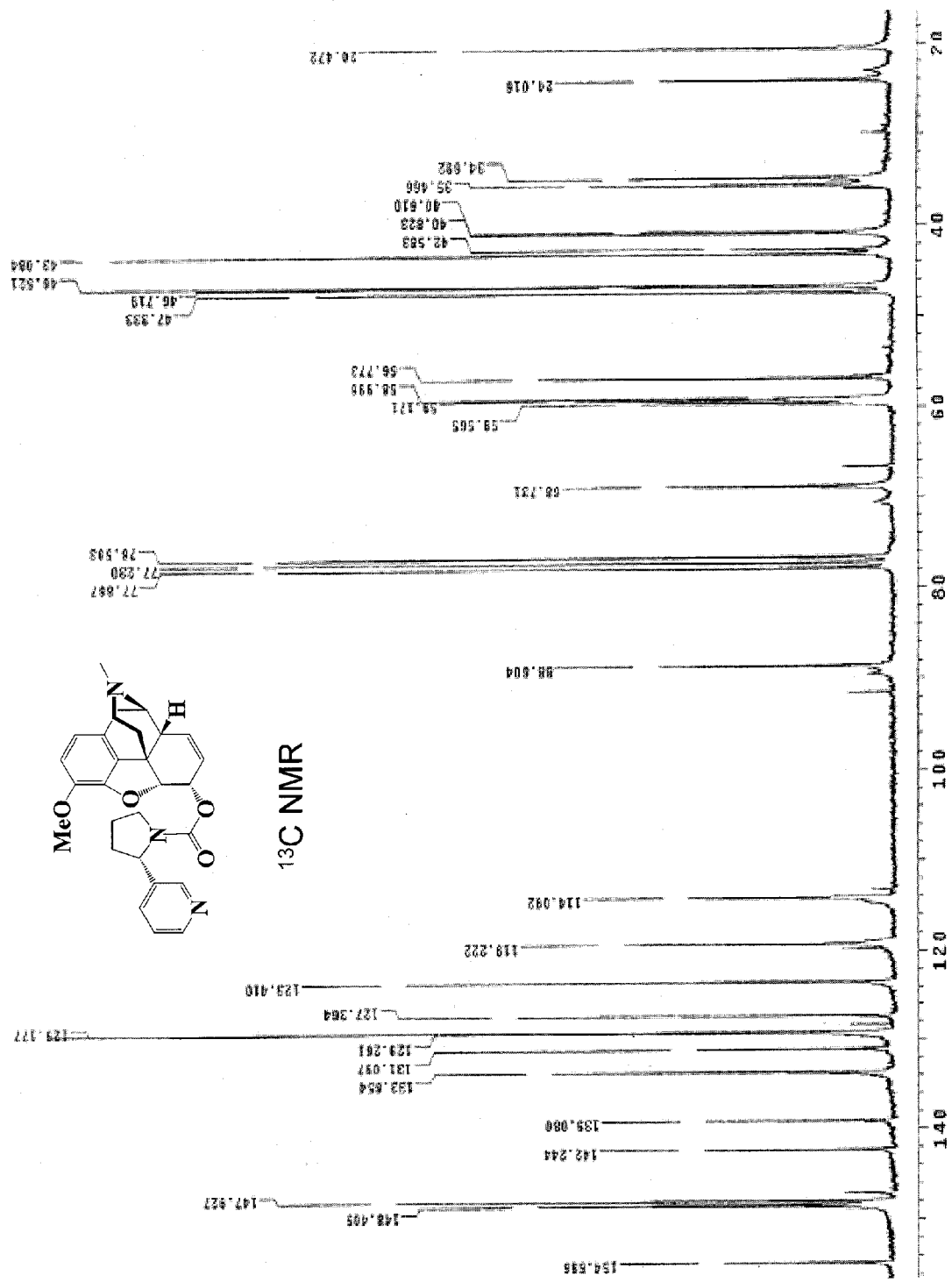
FIG. 15 shows C-NMR analysis of a codrug of codeine and S-nornicotine.
Figure 16:
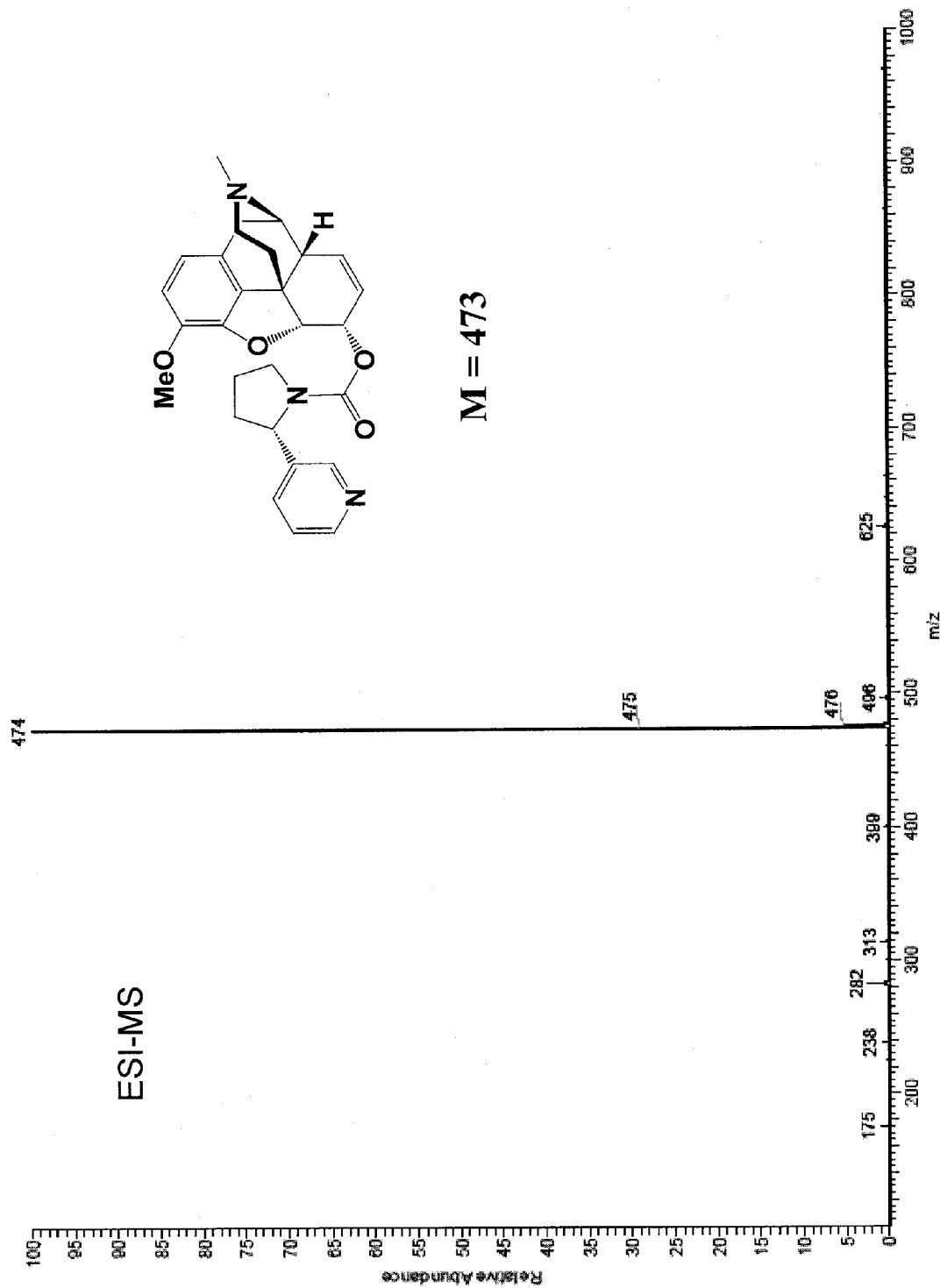
FIG. 16 shows ESI-MS analysis of a codrug of codeine and S-nornicotine.
Figure 17:
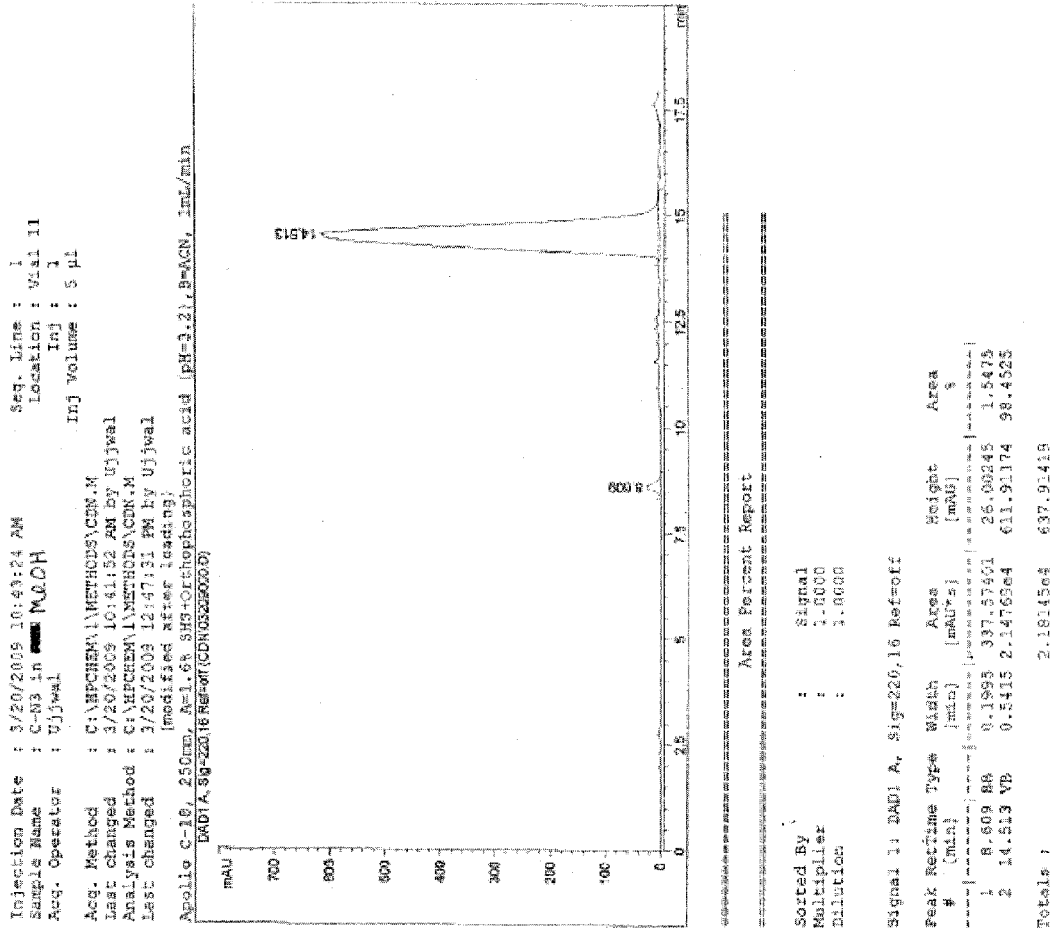
FIG. 17 shows HPLC chromatography of a codrug of codeine and S-nornicotine. The HPLC conditions were as follows: Apollo C-18, 5μ, 4.6×250 mm; Injection Volume=5 μL, 1 mL/min, λ=220 nm; Solvent A=0.16% SHS+Ortho-Phosphoric acid (pH=3.2); Solvent B=Acetonitrile; Use of Gradient system: 0-5 min: 25% B; 5-7 min: 25% 0 31% B; 7-16 min: 31% B; 16-18 min: 31% 0 25% B; 18-20 min: 25% B; SHS=1-heptanesulfonic acid sodium salt.
Figure 18:
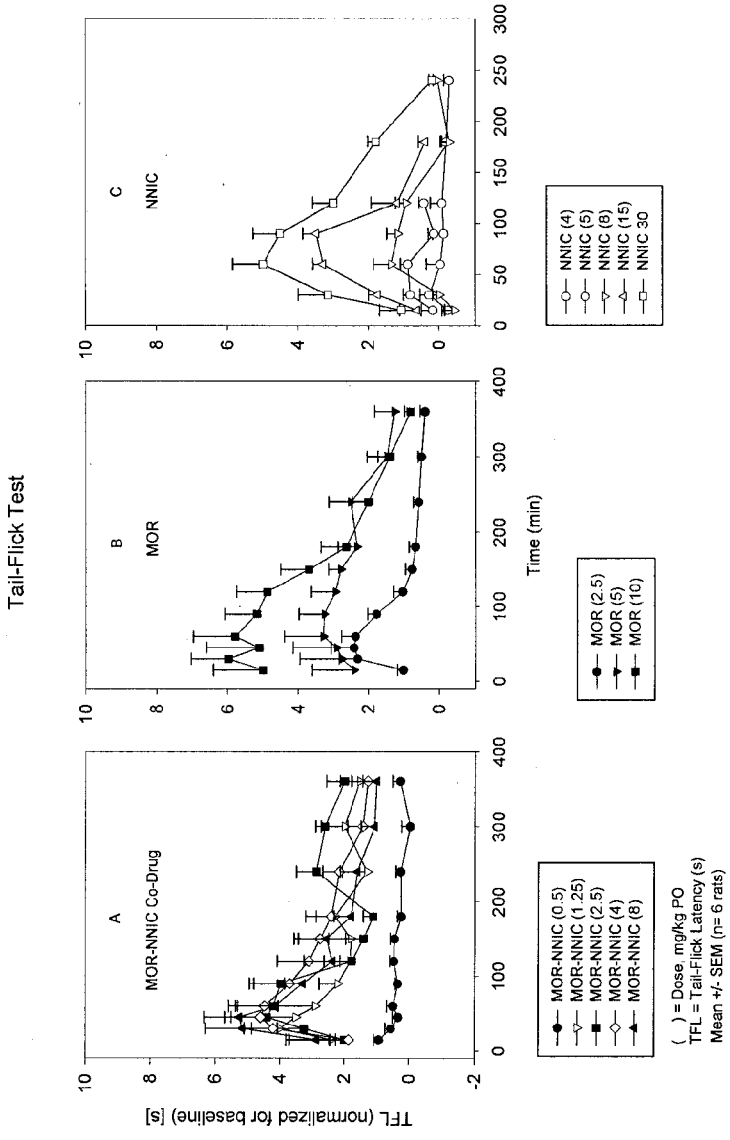
FIG. 18 shows graphs showing the antinociceptive effects of acetylmorphine-S-nornicotine drug following oral administration in rat. Panel 19A shows the effects of the acetylmorphine-S-nornicotine codrug. Panel 19B shows the results of acetylmorphine alone, and Panel 19C shows the effects of S-nornicotine alone.
Figure 19:
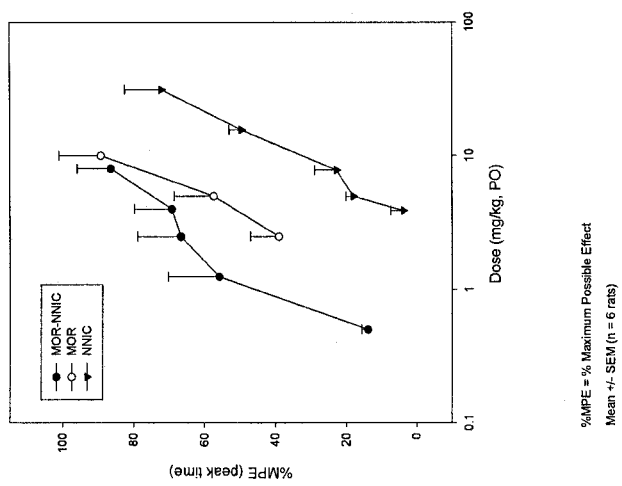
FIG. 19 shows the antinociceptive effects of acetylmorphine-S-nornicotine codrug, as compared to acetylmorphine alone and S-nornicotine alone, using the tail flick test.

Embodiments of the present invention include novel synergistic opioid-nornicotine codrug combinations. Additional embodiments include methods of treating and preventing pain in a subject, comprising administration of a codrug combination of the present invention, as well as methods of synthesizing the codrugs.

By "opioid" is meant any agent that binds to opioid receptors, found principally in the central nervous system and gastrointestinal tract. There are four broad classes of opioids: endogenous opioid peptides, produced in the body; opium alkaloids, such as morphine (the prototypical opioid) and codeine; semi-synthetic opioids such as heroin and oxycodone; and fully synthetic opioids such as pethidine and methadone that have structures unrelated to the opium alkaloids.

In accordance with this detailed description, the following abbreviations and definitions apply. It must be noted that as used herein, the singular forms "a", "an", and "the" include plural referents unless the context clearly dictates otherwise. Thus, for example, reference to "compounds" includes a plurality of such compounds and reference to "the dosage" includes reference to one or more dosages and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Unless otherwise stated, the following terms used in the specification and claims have the meanings given below:

"Pharmaceutically acceptable carrier" means a carrier that is useful in preparing a pharmaceutical composition that is generally safe, non-toxic and neither biologically nor otherwise undesirable, and includes a carrier that is acceptable for human pharmaceutical use as well as veterinary use. "A pharmaceutically acceptable carrier" as used in the specification and claims includes both one and more than one such carrier.

As used herein, a "mammal" or "individual" refers to humans or animals such as dogs, cats, horses and the like and farm animals such as cows, pigs, guinea pigs and the like.

"Treating" or "treatment" of a disease and/or pain includes:

(1) preventing the disease/pain, i.e., causing the clinical symptoms of the disease not to develop in a mammal (preferable a human) that may be exposed to or predisposed to the disease but does not yet experience or display symptoms of the disease, (2) inhibiting the disease/pain, i.e., arresting or reducing the development of the disease or its clinical symptoms, or (3) relieving the disease/pain, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Pharmaceutically acceptable salt" refers to pharmaceutically acceptable salts of nornicotine which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, fumarate, mesylate, acetate, maleate, oxalate and the like.

"Optional" or "optionally" means that the subsequently described event or circumstance may, but need not, occur, and that the description includes instances where the event or circumstance occurs and instances in which it does not.

The term "subject in need thereof" refers to any animal in need of relief from pain, or the same or similar symptoms caused by any other disease or condition. Preferably, the subject is a mammal. More preferably, the subject is human.

"Synergistic effect" and "supra-additive effect" refer to action of two agents such as drugs or chemicals producing an effect, in this case, analgesia, which is greater than the simple addition of the effects of each drug administered by themselves.

"Mammal" or "individual" refers to humans or animals such as dogs, cats, horses, and the like, and farm animals, such as cows, pigs, guinea pigs and the like.

As used herein, (including the claims), the term alkylene or alkylene group is to be understood in the broadest sense to mean hydrocarbon residues which can be linear, i.e., straight-chain, or branched, and can be acyclic or cyclic residues or comprise any combination of acyclic and cyclic subunits. Further, the term alkylene as used herein expressly includes saturated groups as well as unsaturated groups which latter groups contain one or more, for example, one, two, or three, double bonds and/or triple bonds. The term alkylene includes substituted and unsubstituted alkylene groups; one or more carbons may be replaced with heteroatoms O or S; and the alkylene may be pegylated. In accordance with the above substitutions, the alkylene is also understood to include all isomers, diastereiomers, enantiomers; and cis and trans geometrical isomers.

Examples of alkylene residues containing from 1 to 20 carbon atoms are methylene, ethylene, propylene, butylene, pentylene, hexylene, heptylene, octylene, nonylene, decylene, undecylene, dodecylene, tetradecylene, hexadecylene, octadecylene, and eicosylene, the n-isomers of all these residues, isopropylene, isobutylene, 1-methylbutylene, isopentylene, neopentylene, 2,2-dimethylbutylene, 2-methylpentylene, 3-methylpentylene, isohexylene, 2,3,4-trimethylhexylene, isodecylene, sec-butylene, tertbutylene, or tertpentylene. In certain preferred embodiments, the alkylene contains from 1 to 4 carbons.

Unsaturated alkylene residues are, for example, alkenylene residues such as vinylene, 1-propenylene, 2-propenylene (=allyl), 2-butenylene, 3-butenylene, 2-methyl-2-butenylene, 3-methyl-2-butenylene, 5-hexenylene, or 1,3-pentadienylene, or alkynylene residues such as ethynylene, 1-propynylene, 2-propynylene (=propargyl), or 2-butynylene. Alkylene residues can also be unsaturated when they are substituted.

Unless stated otherwise, the term alkylene preferably comprises acyclic saturated hydrocarbon residues containing from 1 to 6 carbon atoms which can be linear or branched. Additionally, included are acyclic unsaturated hydrocarbon residues containing from 2 to 6 carbon atoms which can be linear or branched like (C2-C6)-alkenylene and (C2-C6)-alkynylene, and cyclic alkylene groups containing from 3 to 8 ring carbon atoms, in particular from 3 to 6 ring carbon atoms. A particular group of saturated acyclic alkylene residues is formed by (C1-C4)-alkylene residues like methylene, ethylene, n-propylene, isopropylene, n-butylene, isobutylene, sec-butylene, and tert-butylene.

The present invention provides codrugs, compositions and synthetic methods wherein an opioid analgesic, such as morphine or codeine, and nornicotine, or one of its enantiomers, are combined to produce a single chemical codrug entity. It is administered in amounts to produce a synergistic (greater than additive) analgesic response to pain. The pain may be acute, chronic, or cancer related. The codrugs of the present invention have a slower rate of development of opioid tolerance and dependence, with diminished clinical side effects than those seen with opioid-only therapies for pain. Typical side effects known to occur following the administration of a nicotinic agonist such as nornicotine are also diminished while retaining analgesic activity.

The spectrum of treatable pain symptoms include nociceptive pain, such as low back pain and postsurgical pain, and neuropathic pain, such as diabetic neuropathy and AIDs related neuropathy. These pain symptoms are more effectively treated using the codrugs of the present invention more effectively than by treatment with opioids only.

The codrug of the present invention comprises two different drugs, which when combined have a synergistic analgesic effect in the form of a single chemical entity. The two drugs are connected directly or by means of a cleavable covalent linker, such as an ester, an amide, and a carbamate, which is cleaved in vivo to regenerate the individual drug entities at the desired site of action.

Nicotine has been considered for the treatment of pain, and exhibited strong activity in preclinical animal studies [Aceto M. D. et al., "Antinociceptive action of nicotine and its methiodide derivatives in mice and rats" Br J Pharm (1983) 79: 869-876; Carsten E. et al., "Analgesia induced by chronic nicotine infusion in rats: Differences by gender and pain test" Psychopharmacology (2001) 157: 40-45; Damaj M. I. et al., "Nicotine-induced antinociception in mice: Role of G-proteins and adenylate cyclase" Pharm Biochem Behav (1994) 48: 37-42; Sahley T. L, Bernston G. G. "Antinociceptive effects of central and systemic administration of nicotine in the rat" Psychopharmacology (1979) 65: 279-283; Tripathy H. L. "Nicotine-induced antinociception in rats and mice: Correlation with nicotine brain levels" J Pharmacol Exp Ther (1982) 221: 91-96] and clinical pain study [Flood P., Daniel D. "Intranasal nicotine for postoperative pain treatment" Anesthesiology (2004) 101:1417-1421]. Issues related to nicotine toxicity (seizures, gastrointestinal, respiratory, and motor effects) make nicotine an undesirable analgesic agent.

Nornicotine is the primary metabolite of nicotine, and it also binds to nAChR's. Nornicotine is preferred over nicotine as an analgesic agent, as nornicotine displays a longer half life and a far better side-effect profile than nicotine. Evidence suggests that the pharmacological profile of nornicotine resembles that of nicotine. However, in general, nornicotine has less toxicity than nicotine. Also, nornicotine is less potent than nicotine with regard to its dependence-producing properties [Bardo M. T. et al., "S(−)-Nornicotine partially substitutes for R(+) amphetamine in a drug discrimination paradigm in rats" Pharmacol Biochem Behav (1997) 58: 1083-1087; Bardo M. T. et al., "Nornicotine is self-administered intravenously by rats" Psychopharmacology (1999) 146: 290-296; Green T. A. et al., "Nornicotine pretreatment decreases intravenous nicotine self-administration" Psychopharmacology (2000) 152: 289-294; Risner M. E. et al., "Effects of nicotine, cocaine, and some of their metabolites on schedule controlled responding by beagle dogs and squirrel monkeys" J Pharmacol Exp Ther (1985) 234: 113-119; Risner M. E. et al., "Effects of stereoisomers of nicotine and nornicotine on schedule controlled responding and physiological parameters of dogs" J Pharmacol Exp Ther (1988) 244: 807-813], behavioral sensitization [Dwoskin et al., 1999] and with respect to its cardiovascular effect [Mattila M. "Pharmacological properties of some pyrrolidine N-substituted nornicotine derivatives" Ann Med Exp Biol Fenn (1963) 41: 1-92].

Nornocotine is detectable in the urine from smokers and nicotine-treated laboratory animals. Metabolism of nicotine to nornicotine via N-demethylation is a minor pathway in the periphery [Cundy K. C. et al., "High performance liquid chromatographic method for the determination of N-methyl metabolites of nicotine" J Chromatogr Biomed Appl (1984) 306: 291-301], while formation of nornicotine appears to be a major metabolic route in the central nervous system [Crooks P. A. et al., "Determination of nicotine metabolites in rat brain after peripheral radiolabeled nicotine administration: detection of nornicotine" Drug Metab Disp (1995) 23: 1175-1177; Crooks P. A. et al., "Contribution of CNS nicotine metabolites to the neuropharmacological effects of nicotine and tobacco smoking" Biochem Pharmacol (1997) 54: 743-753; Crooks et al., "Metabolites of nicotine in rat brain after peripheral nicotine administration: cotinine, nornicotine and nicotine" Drug Metab Dispos (1997) 25: 47-54]. Nornicotine has a substantially longer plasma half-life compared to nicotine in humans (8 hours for nornicotine versus 1 hour for nicotine) [Kyerematen G. A. et al., "Disposition of nicotine and eight metabolites in smokers and non-smokers: identification in smokers of two metabolites that are longer lived than cotinine" Clin Pharmacol Ther (1990) 48: 641-651]. Nornicotine resides about 3 times longer than nicotine (166 minutes vs. 52 minutes) in the rat's brain following peripheral administration of nicotine [Ghosheh et al., 1999]. Furthermore, nornicotine accumulates in the brain (about 4-fold compared to nicotine) following repeated nicotine dosing [Ghosheh et al., 2001]. Nornicotine also has superior bioavailability over that of nicotine, which is only 10% orally bioavailable.

Nornicotine appears to be less potent than nicotine with respect to its discriminative stimulus effects [Bardo et al., 1997], reinforcement [Bardo M. T. et al., 1999], its effects on schedule controlled operant responding [Risner et al., 1995], suppression of nicotine self-administration [Green et al., 2000] and behavioral sensitization [Dwoskin et al., 1999]. Blood pressure and autonomic side effects of nornicotine in cats and rats were less pronounced compared to nicotine [Mattila 1963; Stairs et al., (in press)]. The pharmacokinetic profile (accumulation in brain, long half-life, oral availability) and diminished side effect profile make nornicotine and/ or its enantiomers viable candidates as agents for combination with opioids for the treatment of pain.

Studies suggest that nornicotine produces stereoselective effects on locomotor activity, schedule-controlled operant responding, abuse liability and autonomic side effects [Dwoskin et al., 1999; Risner et al., 1988; Stairs et al., (in press)]. This suggests that it may be possible to separate the desirable effect (analgesic) from the undesirable side effects of this nicotinic receptor agonist.

The structures of R- and S-nornicotine are presented below:

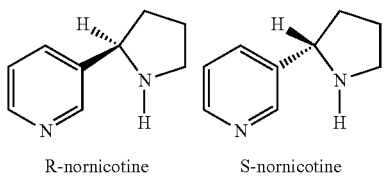

R-nornicotine    S-nornicotine

The codrugs of the present invention have a slower rate of opioid tolerance development and dependence with diminished clinical side effects than typically observed with conventional opioid only therapy for pain. Typical side effects known to occur following administration of nornicotine are also expected to be diminished.

Codrugs of the present invention comprise an opioid and a nornicotine within a single chemical entity. The two drugs may be connected directly or by means of a cleavable covalent linker (e.g., ester, carbonate, amide, carbamate, etc.) which is cleaved in vivo upon administration to regenerate the active drug entities. By providing two drugs as a single entity, instead of as a physical mixture, the codrugs of the present invention provide advantages including improved drug stability, improved targeting of drugs to the site of action and a more desirable pharmacokinetic properties. This is especially true for drugs with differing physiochemical properties, such as lipid solubility.

When the opioid and the nornicotine are linked together and administered as a co-drug, these molecules would undergo the same pharmacokinetics prior to cleavage. Specifically, where different molecules have substantially different partition coefficients, absorption across membranes would be the same. Other advantages of administering different molecules as co-drugs is described in *Synthesis and Hydrolytic Behavior of Two Novel Tripartate Codrugs of Naltrexone and 6β-Naltrexone with Hydroxybupropion as Potential Alcohol Abuse and Smoking Cessation Agents*, Hamad et al., *Bioorganic and Medicinal Chemistry*, 2006, volume 14, pages 7051-7061; the disclosure of which is hereby incorporated by reference in its entirety.

The present invention provides a codrug of the formula:

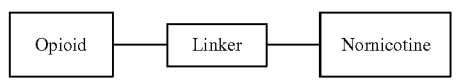

Suitable linkers may include, but are not limited to:

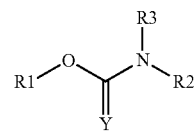

wherein Y is O or S;

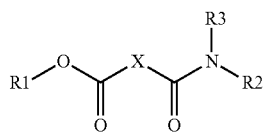

wherein X is nothing, O, S, NH, NR4 (where R4=alkyl), $(CH_2)$ (where x=1-20, and alkyl is linear or branched), and wherein R1-O is an opioid moiety and R2-N—R3 is a nornicotine moiety.

Embodiments of the present invention may include compositions of the following formulae:

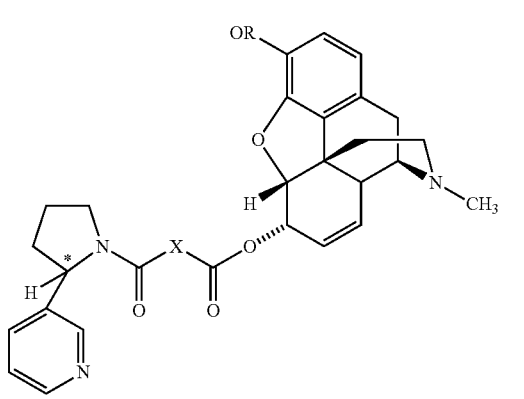

Ia and compositions thereof, wherein X is a bond, O, S, NH, NR4 (where R4=alkyl), $(CH_2)_x$ (where x=1-20, and alkyl is linear or branched), and wherein R=H, $CH_3$, R1-CO— (where R1=alkyl); and * indicates a racemic, S- or R-nornicotine moiety.

Another embodiment of the present invention is a composition of the following formula:

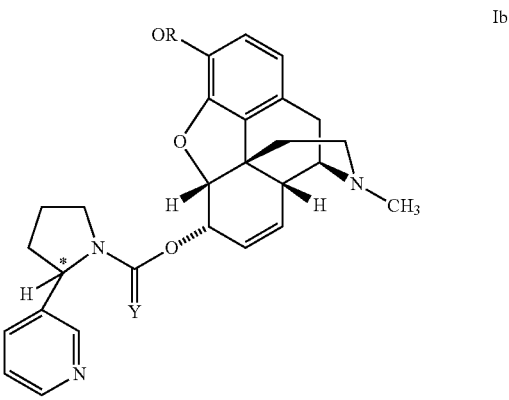

Ib and compositions thereof, wherein Y=O, S; R=H, CH₃, R1-CO— (where R1=alkyl); and * indicates a racemic, S- or R-nornicotine moiety.

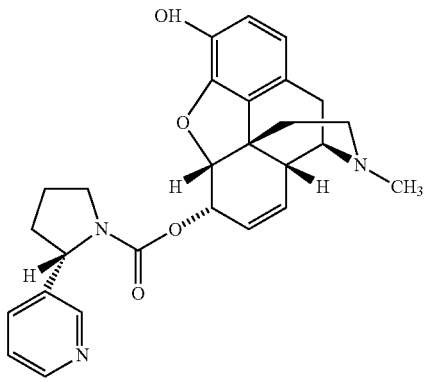

S-nornicotine:morphine codrug

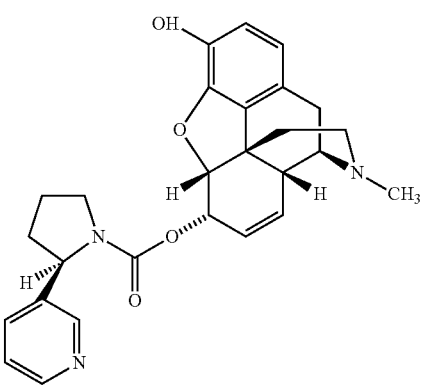

R-nornicotine:morphine codrug

Codrugs of the present invention may include a codrug comprising codeine linked with S-nornicotine as shown:

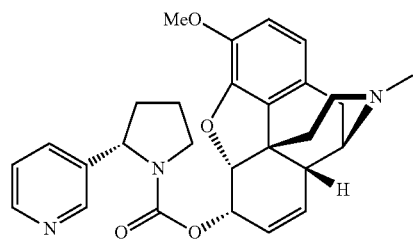

Codrugs of the present invention may also include a codrug comprising 3-acetylmorphine linked with S-nornicotine as shown:

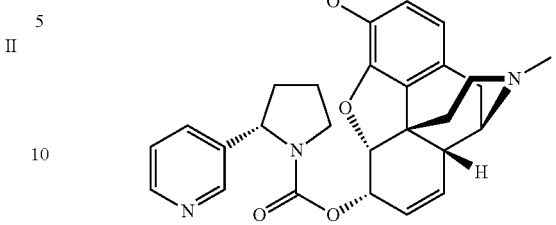

Examples of opioids for combination with nornicotine include all therapeutically useful and pharmacologically active opioids and opioid metabolites and their respective pure enantiomers and/or diastereiomers. Representative examples include but are not limited to dihydroetorphine, butorphanol, pentazocine, morphine, phenazocine, hydromorphone, codeine, oxymorphone, 3-acetylmorphine, methadone, propoxyphene, oxycodone, tramadol, hydrocodone, buprenorphine, levorphanol, dihydrocodeine, L-acetylmethadol, ethylmorphine, nalbuphine, etorphine, buprenorphine, normethadone, dihydromorphine, noroxycodone, normorphine, norlevorphanol, and pharmaceutically acceptable salts, metabolites, enantiomers, diastereiomers and isomers thereof.

Other codrugs may include, but are not limited to, a codrug wherein S-nornicotine is linked to morphine by a carbamate linker; a codrug wherein S-nornicotine is linked to codeine by a carbamate linker; a codrug wherein S-nornicotine is linked to oxycodone by a carbamate linker; a codrug wherein S-nornicotine is linked to 3-acetylmorphine by a carbamate linker; a codrug wherein S-nornicotine is linked to oxymorphone by a carbamate linker; a codrug wherein S-nornicotine is linked to hydromorphone by a carbamate linker; a codrug wherein S-nornicotine is linked to butorphenol by a carbamate linker; a codrug wherein S-nornicotine is linked to bupernorphine by a carbamate linker; a codrug wherein S-nornicotine is linked to tramadol by a carbamate linker; and a codrug wherein S-nornicotine is linked to levorphanol by a carbamate linker.

In certain embodiments, the general multi-step synthetic procedure for preparation of the codrug includes: reacting para-nitrophenyl chloroformate with an opiate drug containing a hydroxy group in the presence of triethyl amine and dry chloroform and the solution is cooled to 0 degrees C. The resulting 6-O-para-nitrophenoxycarbonate ester of an opiate drug is then reacted with a nornicotine to yield the nornicotine-opioid codrug.

Generally speaking the opioids and nornicotine of the present invention that are synthesized into co-drugs in accordance with the present invention will contain a free hydroxyl group or another equivalent moiety capable of being acylated. Examples of other moieties include primary or secondary amines, or carbonyl containing moieties. Example of opioids suitable for synthesis of the codrugs in accordance with the present invention include dihydroetorphine, butorphanol, pentazocine, morphine, phenazocine, hydromorphone, codeine, oxymorphone, 3-acetylmorphine, methadone, propoxyphene, oxycodone, tramadol, hydrocodone, buprenorphine, levorphanol, dihydrocodeine, L-acetylmethadol, ethylmorphine, nalbuphine, etorphine, buprenorphine, normethadone, dihydromorphine, noroxycodone, normorphine, norlevorphanol, and pharmaceutically acceptable salts, metabolites, enantiomers, diastereiomers and isomers thereof.

S-nornicotine, R-nornicotine, and racemic nornicotine are suitable for use in the present invention.

Compositions of the present invention can be synthesized using the methods readily available to the skilled artisan, including those methods known in the art of synthetic organic chemistry, or variations thereon as readily appreciated and readily performable by those skilled in the art. Moreover, the synthesis methods known in the art are not intended to comprise a comprehensive list of all means by which the compositions described and claimed in this patent application may be synthesized. Some of the compounds of the invention may have stereogenic centers. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diasteriomeric mixture of isomers. Thus, when using the term "compound", it is understood that all stereoisomers are included.

The compounds of the present invention may be obtained or used as inorganic or organic salts using methods known to those skilled in the art. It is well known to one skilled in the art that an appropriate salt form is chosen based on physical and chemical stability, flowability, hydroscopicity and solubility. Pharmaceutically acceptable salts of the present invention with an acidic moiety may be optionally formed from organic and inorganic bases. For example with alkali metals or alkaline earth metals such as sodium, potassium, lithium, calcium, or magnesium or organic bases and N-tetraalkylammonium salts such as N-tetrabutylammonium salts. Similarly, when a compound of this invention contains a basic moiety, salts may be optionally formed from organic and inorganic acids.

For example salts may be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids. The compounds can also be used in the form of esters, carbamates and other conventional prodrug forms, which when administered in such form, convert to the active moiety in vivo. When using the term "compound" herein, it is understood that all salts are included.

The term "pharmaceutically acceptable salt" as used herein is intended to include the non-toxic acid addition salts with inorganic or organic acids, e.g. salts with acids such as hydrochloric, phosphoric, sulfuric, maleic, acetic, citric, succinic, benzoic, fumaric, mandelic, p-toluene-sulfonic, methanesulfonic, ascorbic, lactic, gluconic, trifluoroacetic, hydroiodic, hydrobromic, and the like. Examples of pharmaceutically acceptable salts include, but are not limited to, mineral or organic acid salts of basic residues such as amines; alkali or organic salts of acidic residues such as carboxylic acids; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference in its entirety.

The codrugs and compositions and formulations thereof effective compounds may be administered alone or in conjunction with other pharmaceutically active compounds. It will be understood by those skilled in the art that pharmaceutically active compounds to be used in combination with the compounds described herein will be selected in order to avoid adverse effects on the recipient or undesirable interactions between the compounds. As used herein, the term "active ingredient" or "active agent" is meant to include compounds described herein when used alone or in combination with one or more additional pharmaceutically active compounds. The amount of the compounds described herein required for use in the various treatments of the present invention depend, inter alia, on the route of administration, the age and weight of the animal (e.g. human) to be treated and the severity of the condition being treated.

The compositions of the present invention and such second therapeutic agent can be administered separately or as a physical combination in a single dosage unit, in any dosage form and by various routes of administration, as described above. The compositions of the present invention may be formulated together with the second therapeutic agent in a single dosage unit (that is, combined together in one dosage form). When the compositions of the present invention and the second therapeutic agent are not formulated together in a single dosage unit, they may be administered essentially at the same time, or in any order; for example, the compositions of the present invention may be administered first, followed by administration of the second agent.

It is desireable to administer the codrugs of the present invention as pharmaceutical formulations. Useful formulations comprise a codrug and one or more pharmaceutically acceptable carriers. Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985).

Suitable routes of administering the pharmaceutical preparations include, for example, oral, rectal, topical (including transdermal, dermal, buccal and sublingual), vaginal, parenteral (including subcutaneous, intramuscular, intravenous, intradermal, intrathecal and epidural) and by nasogastric tube.

In general, the codrugs of the subject invention will be administered in a therapeutically effective amount by any of the accepted modes of administration for agents that serve similar utilities. Such compositions are prepared in a manner well known in the pharmaceutical art. In one probable mode of administration, the codrug will be administered by the oral route.

The actual amount of the codrug will depend on a number of factors, such as the severity of the pain to be treated, the age and relative health of the subject, the potency of the agent used, the route and form of administration, and other factors. Toxicity and therapeutic efficacy of such compounds can be determined by standard pharmaceutical procedures in vitro or in experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Data obtained in vitro and in animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. A dose may be formulated in animal models to achieve a circulating plasma concentration range which includes the $ED_{50}$ (i.e., the dose of the test compound which achieves a half-maximal inhibition of symptoms). Such information can be used to more accurately determine useful doses in humans. Levels in plasma may be measured, for example, by high performance liquid chromatography.

In preparing the compositions of this invention, the codrug may be mixed with an excipient, diluted by an excipient or enclosed within a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The quantity of codrug in the pharmaceutical composition and unit dosage form thereof may be varied or adjusted widely depending upon the particular application, the manner or introduction, the potency of the particular compound, and the desired concentration. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The codrug is effective over a wide dosage range and is generally administered in a pharmaceutically or therapeutically effective amount. It will be understood, however, that the amount of the codrug actually administered will be determined by a physician, in the light of the relevant circumstances, including the condition to be treated, the severity of the disease being treated, the chosen route of administration, the actual compound administered, the age, weight, and response of the individual patient, the severity of the patient's symptoms, and the like. Typically, the physician will administer the compound until a dosage is reached that achieves the desired effect.

The codrugs of the invention will be administered in a therapeutically effective amount by any of the accepted modes of administration. The codrugs can be administered by a variety of routes, including, but not limited to, oral, parenteral (e.g., subcutaneous, intravenous, intramuscular, intraperitoneal, intraarterial), intralesional, neuroaxial (epidural, intrathecal, intracerebral), topical, intranasal, localized (e.g., surgical application or surgical suppository), sublingual, submucosal, rectal, vaginal, pulmonary (e.g., aerosols, inhalation, or powder) and transdermal routes of administration. The compounds can be administered continuously by infusion or by bolus injection. Such compositions are prepared in a manner well known in the pharmaceutical art.

The actual amount of the codrug of the subject invention will depend on a number of factors, such as the severity of the pain and/or condition, i.e., the condition or disease to be treated, the age and relative health of the subject, the potency of the compound used, the route and form of administration, and other factors. The amount of the pharmaceutical composition administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending physician depending upon factors such as the severity of the pain, the age, weight and general condition of the patient, and the like.

The compositions administered to a patient are in the form of pharmaceutical compositions described supra. These compositions may be sterilized by conventional sterilization techniques, or may be sterile filtered. When employed as pharmaceuticals, the compounds of the subject invention are usually administered in the form of pharmaceutical compositions. This invention also includes pharmaceutical compositions, which contain as the active ingredient, one or more of the compounds of the subject invention above, associated with one or more pharmaceutically acceptable carriers or excipients. The excipient employed is typically one suitable for administration to human subjects or other mammals.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and/or flavoring agents. By way of example, for preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. The compositions of the invention can be formulated so as to provide rapid, sustained or delayed release of the active ingredient after administration to the patient by employing procedures known in the art.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, alcohol, and cellulose acetate.

The preferred parenteral form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or non-toxic, nontherapeutic, nonimmunogenic stabilizers and the like. Also included may be carrier molecules such as proteoglycans. Specific examples of such carrier molecules include, but are not limited to, glycosaminoglycans such as heparin sulfate, hyaluronic acid, keratan-sulfate, chondroitin 4-sulfate, chondroitin 6-sulfate, heparan sulfate and dermatin sulfate, perlecan, and pento polysulfate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. The compositions may be administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472, which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The codrugs of this invention may be administered in a sustained release form. Suitable examples of sustained-release preparations include semipermeable matrices of solid hydrophobic polymers, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.* 15: 167-277 (1981) and Langer, *Chem. Tech.* 12: 98-105 (1982) or poly(vinyl alcohol)), polylactides (U.S. Pat. No. 3,773,919), copolymers of L-glutamic acid and gamma ethyl-L-glutamate (Sidman et al., *Biopolymers* 22: 547-556, 1983), non-degradable ethylene-vinyl acetate (Langer et al., supra), degradable lactic acid-glycolic acid copolymers such as the LUPRON DEPOT™ (i.e. injectable microspheres composed of lactic acid-glycolic acid copolymer and leuprolide acetate), and poly-D-(−)-3-hydroxybutyric acid (EP 133,988). The compounds of this invention can be administered in a sustained release form, for example a depot injection, implant preparation, or osmotic pump, which can be formulated in such a manner as to permit a sustained release of the active ingredient. Implants for sustained release formulations are well-known in the art. Implants may be formulated as, including but not limited to, microspheres, slabs, with biodegradable or non-biodegradable polymers. For example, polymers of lactic acid and/or glycolic acid form an erodible polymer that is well-tolerated by the host. The implant is placed in proximity to the site of protein deposits (e.g., the site of formation of amyloid deposits associated with neurodegenerative disorders), so that the local concentration of active agent is increased at that site relative to the rest of the body.

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka et al., U.S. Pat. Nos. 4,235,871, 4,501,728 and 4,837,028 each of which is incorporated herein by reference.

In the formulations and methods of the present invention, the inventive compositions can form the active ingredient, and are typically administered in admixture with suitable pharmaceutical diluents, excipients, or carriers (collectively referred to herein as carrier materials) suitably selected. Compositions of the present invention may also be coupled with soluble polymers as targetable drug carriers. Furthermore, the compositions of the present invention may be coupled to a class of biodegradable polymers useful in achieving controlled release of a drug, for example, polylactic acid, polyglycolic acid, copolymers of poly lactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

For pharmaceutical use, the compounds described herein may be taken up in pharmaceutically acceptable carriers, such as, for example, solutions, suspensions, tablets, capsules, ointments, elixirs and injectable compositions. In certain embodiments of the invention, pharmaceutical preparations may contain from 0.1% to 99.9% by weight of active ingredient. Certain examples of preparations in accordance with the present invention which are in single dose form, "unit dosage form", may contain from 20% to 90% active ingredient, and certain preparations of the present invention which are not in single dose form may contain from 5% to 50% active ingredient. As used herein, the term "active ingredient" refers to compounds described herein, salts thereof and mixtures of compounds described herein with other pharmaceutically active compounds. In certain embodiments of the invention, dosage unit forms such as, for example, tablets or capsules typically contain from about 0.05 to about 1.0 g of active ingredient.

The method of the present invention includes administering the effective compounds described herein to people or animals by any route appropriate as determined by one of ordinary skill in the art. Additionally, physiologically acceptable acid addition salts of compounds described herein are also useful in the methods of treating of the present invention. Other aspects of the present invention relate to methods of inhibiting pain initiation or signaling in a mammal having a painful response. The methods of the present invention generally comprise administering a pharmaceutically or therapeutically effective amount of a composition as described herein to a patient in need of such treatment whereby pain signaling is inhibited. The patient may be a mammal, preferably a human. For example, a patient will need treatment when exhibiting a painful response in the course of a disease or traumatic condition. Such need is determinable by skilled clinicians and investigators in the medical arts. Additionally, the compounds of the present invention may be used as part of a method of managing pain, or preventing pain prior to, for example, a medical procedure.

Routes of Administration

In aspects of the present invention, the compositions may be administered at the site of perceived pain in a topical, subcutaneous or intramuscular form, using dosage forms well known or readily determinable to those of skill in the pharmaceutical arts. The compositions of the present invention can be administered by any means that produces contact of the active agent with the agent's site of action in the body of a mammal, i.e., the site of pain.

The compositions for the present invention can also be administered in intranasal form via topical use of suitable intranasal vehicles.

It will be understood by those skilled in the art that the preferred route of administration will depend upon the condition being treated and may vary with factors such as the condition of the recipient.

In certain embodiments, administration of the compositions of the present invention may be for either a prophylactic or therapeutic use. When provided prophylactically, a compound of the present invention is provided in advance of exposure to conditions indicative of the methods of treatment of the present invention. For example, the compounds of the present invention may be used in advance of a medical procedure believed to produce a pain response.

The dosage when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above. The proper dosage of a composition of the present invention when administered in combination with the second therapeutic agent will be readily ascertainable by a medical practitioner skilled in the art, once armed with the present disclosure. Upon improvement of a patient's condition, a maintenance dose of a composition of the present invention may be administered, if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of pain.

The compounds recited herein are presented for exemplary purposes only, and should not be construed as being a limited presentation of compounds of the present invention.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the Specification and Examples be considered as exemplary only, and not intended to limit the scope and spirit of the invention.

Unless otherwise indicated, all numbers expressing quantities of ingredients, properties such as reaction conditions, and so forth used in the Specification and Claims are to be understood as being modified in all instances by the term "about." Accordingly, unless indicated to the contrary, the numerical parameters set forth in the Specification and Claims are approximations that may vary depending upon the desired properties sought to be determined by the present invention.

Notwithstanding that the numerical ranges and parameters setting forth the broad scope of the invention are approximations, the numerical values set forth in the experimental or example sections are reported as precisely as possible. Any numerical value, however, inherently contain certain errors necessarily resulting from the standard deviation found in their respective testing measurements.

EXAMPLES

Example 1

Preparation of 3-Acetylmorphine-S-Nornicotine Codrug

Procedure for Preparing Morphine Free Base.

1 g (2.64 mmol) of morphine sulfate was dissolved in 100 mL of distilled water and then $NaHCO_3$ (3.79 g, 45 mmol) was added. Morphine free base precipitated out. Precipitated morphine free base was then filtered and left to dry overnight in a dessicator under partial vacuum. 0.613 g (81% yield).

Procedure for the Synthesis of 3-acetylmorphine.

To a suspension of morphine (0.5 g, 1.75 mmol) in saturated $NaHCO_3$ solution (25 mL), acetic anhydride (0.5 mL, 5.25 mmol) was added dropwise and allowed to stir for 3 hours. Progress of the reaction was monitored by TLC and after the completion; reaction mixture was extracted 6 times with dichloromethane. Dichloromethane layers were combined, dried over anhydrous sodium sulfate, filtered and concentrated under vacuum to get solid 3-acetylmorphine. 0.34 g (59% yield). GC-MS, $^1H$ and $^{13}C$ NMR confirmed the structure.

Scheme 1[a]

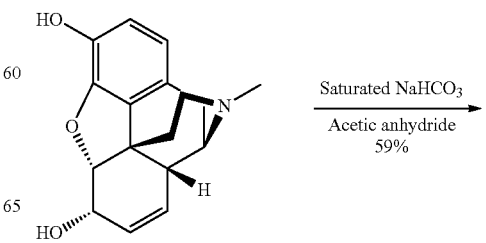

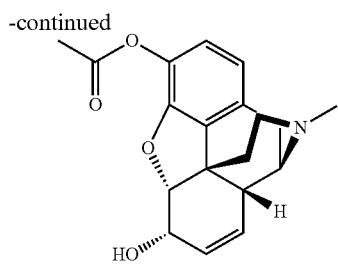

Procedure for the Synthesis of para-nitrophenoxycarbonate ester of 3-acetylmorphine.

The synthesis of the codrug involved first conversion of 3-acetylmorphine to a reactive intermediate, para-nitrophenoxycarbonate ester of 3-acetylmorphine and then reacting the carbonate ester with S-nornicotine. In the first step the para-nitrophenoxycarbonate ester of 3-acetylmorphine was prepared. All glassware was oven-dried and cooled under a nitrogen atmosphere. 500 mg (1.53 mmol) of 3-acetylmorphine was placed in a round-bottom flask under a nitrogen atmosphere and was dissolved in 6 mL of dry chloroform. The solution was then cooled to 0° C. in an ice-bath. 224 mg (1.84 mmol) of DMAP was added to the solution and the mixture was allowed to stir for 5 minutes. 371 mg (1.84 mmol) of para-nitrophenyl chloroformate was dissolved in 5 mL of dry chloroform and the solution was added drop-wise to the reaction mixture; the reaction mixture was then allowed to warm to room temperature. The progress of the reaction was monitored by TLC. After the reaction was complete, the reaction mixture was diluted with chloroform and washed 6 times with 50% aqueous NaHCO$_3$ solution to remove the para-nitrophenol side-product and then with brine. The chloroform layer was then dried over anhydrous sodium sulfate, filtered, concentrated under vacuum, and the resulting residue washed with hexanes to afford the para-nitrophenoxycarbonate ester of 3-acetylmorphine as a pale yellow solid in 51% yield. $^1$H-NMR (CDCl$_3$): δ8.3 (2H, dd), 7.46 (2H, dd), 6.8 (1H, d), 6.63 (1H, d), 5.73 (1H, d), 5.52 (1H, d), 5.24 (1H, d), 5.16 (1H, m), 3.43-1.93 (14 H). MS (ESI) m/z 493 (M+H)$^+$.

Procedure for the Synthesis 3-Acetylmorphine-S-Nornicotine Codrug.

In second step, the hybrid drug of 3-acetylmorphine and S-nornicotine was synthesized in the following way. All glassware was oven-dried and then cooled under a nitrogen atmosphere. 148 mg (1 mmol) of S-nornicotine was placed in a round-bottom flask under nitrogen atmosphere and dissolved in 4 mL of dry THF. The solution was cooled to 0° C. in an ice-bath. 44 mg (1.1 mmol) of NaH was added and the mixture was allowed to stir for 5 minutes. 492 mg (1 mmol) of the para-nitrophenoxycarbonate ester of 3-acetylmorphine was dissolved in 6 mL of dry THF and the resulting solution was added dropwise to the reaction mixture; the reaction mixture was allowed to warm to room temperature. The progress of the reaction was monitored by TLC. After the reaction was complete, the reaction mixture was first passed through a pad of celite and then concentrated under vacuum and then diluted with chloroform. The chloroform layer was washed 3 times with 50% aqueous NaHCO$_3$ solution and once with brine. The chloroform layer was dried over anhydrous Na$_2$SO$_4$, filtered, and then concentrated under vacuum to afford the hybrid drug of 3-acetylmorphine and S-nornicotine as an amorphous solid. The codrug was purified using column chromatography to afford 52% yield. $^1$H-NMR (CDCl$_3$): δ8.53-7.22 (4H, m, pyridyl protons), 6.77 (1H, d), 6.59 (1H, d), 5.68 (1H, d), 5.4 (1H, d), 5.02 (2H, m), 3.77-1.86 (21 H).

Scheme 1$^c$ Example 2: Preparation of Codeine-S-Nornicotine codrug

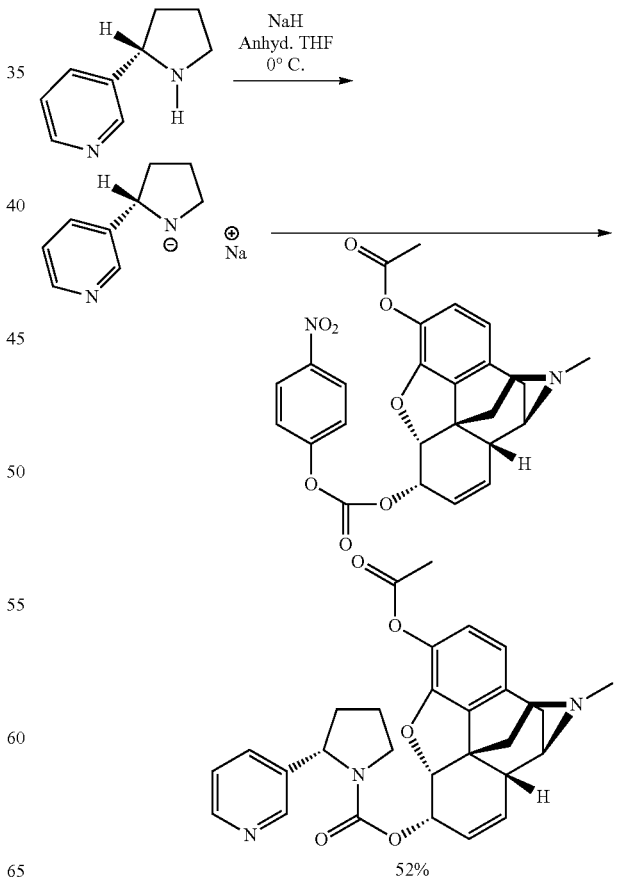

Scheme 1$^b$

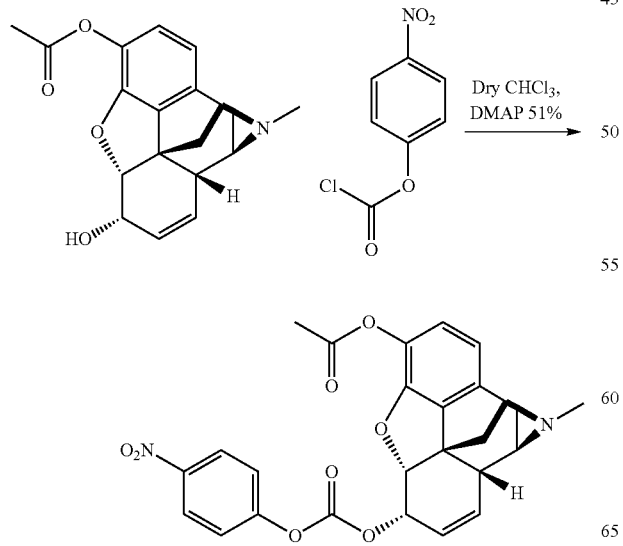

S-Nicotine and 4-Nitrophenylchloroformate were purchased from Sigma-Aldrich Chemical Co.

Procedure for the Synthesis of S-nornicotine.

S-Nicotine free base (6 g, 37 mmol), was added with stirring to a mixture of 0.3 N aqueous sulfuric acid (120 ml) and manganese dioxide (36 g). The mixture was stirred and heated to reflux under a condenser for 10-12 hours. After cooling to room temperature, the mixture was filtered and solid was washed with 0.3 N sulfuric acid (30 ml×2 times) and water (30 ml). The filtrate was washed 5 times with methylene chloride and the resulting aqueous solution was basified with 2.5N NaOH to pH 10-11. The resulting basic mixture was first filtered and then extracted with methylene chloride and then concentrated under reduced pressure to afford S-nornicotine (1.75 g, 32% yield), recovered as an oil. The product showed over 99% purity by GC/MS analysis and HPLC analysis. $^1$H-NMR (CDCl$_3$): δ1.67-1.83 (2H, m, CH$_2$), 1.86-2.23 (2H, m, CH$_2$), 3.06-3.18 (2H, m, CH$_2$), 4.16 (1H, s, NH), 4.18 (1H, t, CH), 7.26-8.46 (4H, m, pyridyl protons) ppm.

Scheme 1$^a$

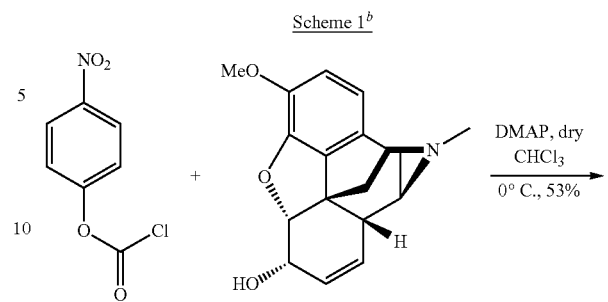

Procedure for Preparing Codeine Free Base.

1 g (2.52 mmol) of codeine phosphate was dissolved in 60 mL of water and then 30% NaOH solution was added dropwise until the pH of the solution reached 10. Codeine free base precipitated out at this pH. Codeine free base was extracted with chloroform 5 times from the aqueous layer. Chloroform layers were combined, dried over anhydrous Na$_2$SO$_4$, filtered and then concentrated under vacuum to get 0.59 g (78% yield) of codeine free base as a white solid.

Procedure for the Synthesis of para-nitrophenoxycarbonate ester of Codeine.

The synthesis of the codrug involved first conversion of codeine to a reactive intermediate, para-nitrophenoxycarbonate ester of codeine and then reacting the carbonate ester with S-nornicotine. In the first step the para-nitrophenoxycarbonate ester of codeine was prepared. All glassware was oven-dried and cooled under a nitrogen atmosphere. 500 mg (1.67 mmol) of codeine was placed in a round-bottom flask under a nitrogen atmosphere and was dissolved in 6 mL of dry chloroform. The solution was then cooled to 0° C. in an ice-bath. 244 mg (2 mmol) of DMAP was added to the solution and the mixture was allowed to stir for 5 minutes. 403 mg (2 mmol) of para-nitrophenyl chloroformate was dissolved in 5 mL of dry chloroform and this solution was added drop-wise to the reaction mixture; the reaction mixture was then allowed to warm to room temperature. The progress of the reaction was monitored by TLC. After the reaction was complete, the reaction mixture was diluted with chloroform and washed 6 times with 50% aqueous NaHCO$_3$ solution to remove the para-nitrophenol side-product and then with brine. The chloroform layer was then dried over anhydrous sodium sulfate, filtered, concentrated under vacuum, and the resulting residue washed with hexanes to afford the para-nitrophenoxycarbonate ester of codeine as a pale yellow solid in 53% yield. $^1$H-NMR (CDCl$_3$): δ 8.3 (2H, dd), 7.48 (2H, dd), 6.7 (1H, d), 6.6 (1H, d), 5.74 (1H, d), 5.53 (1H, d), 5.18 (2H, m), 3.85 (3H, s), 3.46-1.91 (11H). MS (ESI) m/z 465 (M+H)$^+$.

Procedure for the Synthesis Codeine-S-Nornicotine Codrug.

In second step, the hybrid drug of codeine and S-nornicotine was synthesized in the following way. All glassware was oven-dried and then cooled under a nitrogen atmosphere. 148 mg (1 mmol) of S-nornicotine was placed in a round-bottom flask under a nitrogen atmosphere and dissolved in 4 mL of dry THF. The solution was cooled to 0° C. in an ice-bath. 44 mg (1.1 mmol) of NaH was added and the mixture was allowed to stir for 5 minutes. 464 mg (1 mmol) of the para-nitrophenoxycarbonate ester of codeine was dissolved in 6 mL of dry THF and the resulting solution was added dropwise to the reaction mixture; the reaction mixture was allowed to warm to room temperature. The progress of the reaction was monitored by TLC. After the reaction was complete, the reaction mixture was first passed through a pad of celite and then concentrated under vacuum and then diluted with chloroform. The chloroform layer was washed 3 times with 50% aqueous NaHCO$_3$ solution and once with brine. The chloroform layer was dried over anhydrous Na$_2$SO$_4$, filtered, and then concentrated under vacuum to afford the hybrid drug of codeine and S-nornicotine as an amorphous solid. The codrug was purified using column chromatography to afford 61% yield. $^1$H-NMR (CDCl$_3$): δ8.5-7.2 (4H, m, pyridyl protons), 6.65 (1H, d), 6.54 (1H, d), 5.66 (1H, d), 5.3 (1H, d), 5.02 (2H, m), 3.84 (3H, s), 3.75-1.88 (18 H). MS (ESI) m/z 474 (M+H)$^+$.

Scheme 1ᶜ HPLC UV Assay.

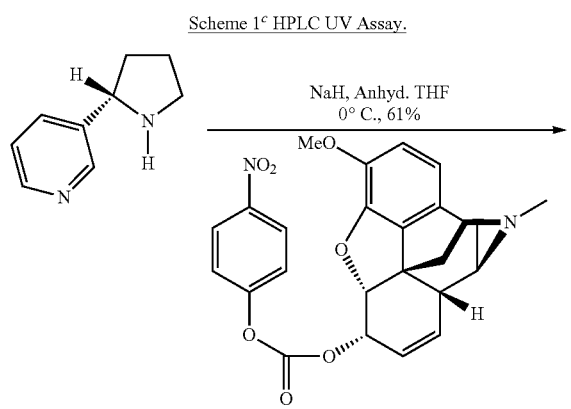

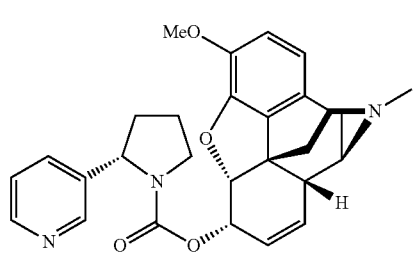

Analysis of the codrug was carried out on an Agilent 1100 Series Quat pump, equipped with an Agilent photodiode array detector. The column was an Apollo $C_{18}$ (5 μm, 4.6×250 mm). The eluents were a solution of 1-heptanesulfonic acid sodium salt (1.6 g) in water (1000 mL), pH adjusted to 3.2 with orthophosphoric acid (=solvent A) and acetonitrile (=solvent B). Elution was performed with the gradient: 0-5 min 75% solvent A; 5-7 min from 75 to 69% solvent A; 7-16 min 69% A; 16-18 min from 69 to 75% A; 18-20 min 75% A. The flow rate was 1 mL/min and the injection volume 5 μL. Codrug elution was monitored at 220 nm.

Example 2

Administration of Nornicotine Perchlorate—Tail Flick Protocol:
Experiment: Tail-Flick—AI at 40%; cut-off 10 sec.
Measurements will be taken at baseline (2×), 5, 10, 15, 30, 45, 60, 90, 120 minutes after drug administration.

Drug Treatment:
10 mg of drug will be administered in a 10 ul vol., followed by a 10 ul saline flush.
Both R- & S-nornicotine will be tested.
Preparation of Solution:
10 ug in 10 ul vol.
100 ug in 100 ul vol.
1000 mg in 1000 ml vol.
1 mg in 1 ml=10 mg/10 ml vol.

Drug Administration Schedule:

| Rat | Day 1 | Day 2 | Day 3 | Day 4 |
|---|---|---|---|---|
| 1 | 10 ul R | R | R | R |
| 2 | 10 ul R | R | R | R |
| 3 | 10 ul R | R | R | R |
| 4 | 10 ul R | R | R | R |
| 5 | 10 ul R | R | R | R |
| 6 | 10 ul S | S | S | S |
| 7 | 10 ul S | S | S | S |
| 8 | 10 ul S | S | S | S |
| 9 | 10 ul S | S | S | S |
| 10 | 10 ul S | S | S | S |

IT—Narnicotine Perchlorate—Day 1
Tail-Flick—IITC Life Science Model 33 Series 8
AI=40% Cutoff=10 sec.

| Inject time | Rat | Dose | Wt. | Baseline | Baseline | 5 min. | 10 min. | 15 min. | 30 min. | 45 min. | 60 min. | 90 min. |
|---|---|---|---|---|---|---|---|---|---|---|---|---|
| 10:10 | 1 | R | 397 | 2.84 | 3.36 | 3.04 | 2.23 | 3.16 | 2.55 | 3.13 | 2.19 | |
| 10:10 | 2 | R | 319 | 4.43 | 4.60 | 5.00 | 4.08 | 4.34 | 3.13 | 2.87 | 2.75 | |
| 10:10 | 3 | R | 357 | 4.22 | 4.35 | 5.47 | 2.53 | 2.82 | 3.90 | 4.26 | 3.12 | |
| 10:10 | 4 | R | 347 | 2.96 | 2.54 | 2.16 | 1.80 | 2.86 | 2.73 | 2.40 | 2.63 | |
| 10:10 | 5 | R | 367 | 4.85 | 3.66 | 6.67 | 5.95 | 2.82 | 4.14 | 4.95 | 3.93 | |
| 11:15 | 6 | S | 366 | 3.90 | 4.14 | 8.17 | 6.21 | 3.29 | 3.47 | 4.60 | 4.26 | |
| 11:15 | 7 | S | 359 | 4.01 | 3.16 | 3.84 | 3.21 | 3.56 | 4.05 | 4.07 | 3.35 | |
| 11:15 | 8 | S | 343 | 4.79 | 4.96 | 9.06 | 6.39 | 4.58 | 6.14 | 3.95 | 4.11 | |
| 11:15 | 9 | S | 350 | 3.84 | 4.07 | 8.01 | 5.47 | 4.33 | 3.31 | 3.57 | 3.35 | |
| 11:15 | 10 | S | 356 | 3.66 | 2.54 | 4.40 | 5.60 | 6.08 | 4.85 | 2.23 | 4.27 | |

Rats 1-5 10:15 10:20 10:25 10:40 10:55 11:10

Rats 6-10 11:20 11:25 11:30 11:45 12:00 12:15

S=0.0010 g in 10 ml saline; 10 ug/10 ul} cover with aluminum foil—

R=0.0010 g in 1 ml saline; 10 ug/10 ul} light sensitive

Behavior:
R—no noticeable side effects

S—no obvious side effects with S either

Saline Control—IT

| Inject Time | Rat | Treatment | Wt. | Baseline | Baseline | 5 min. | 10 min. | 15 min. | 30 min. | 45 min. | 60 min. |
|---|---|---|---|---|---|---|---|---|---|---|---|
| 10:05 | 1 | Sal. | 405 | 2.23 | 2.43 | 2.41 | 2.22 | 2.49 | 1.56 | 1.97 | 1.42 |
| 10:05 | 2 | Sal. | 325 | 2.49 | 2.16 | 2.83 | 3.42 | 2.96 | 1.55 | 2.38 | 3.41 |
| 10:05 | 3 | Sal. | 357 | 2.65 | 2.41 | 2.27 | 2.57 | 2.23 | 1.81 | 2.57 | 1.92 |
| 10:05 | 4 | Sal. | 347 | 3.27 | 2.23 | 1.66 | 1.70 | 2.04 | 2.14 | 2.00 | 1.78 |
| 10:05 | 5 | Sal. | 371 | 2.51 | 2.22 | 2.17 | 2.16 | 2.04 | 1.44 | 2.58 | 1.81 |
| 10:05 | 6 | Sal. | 367 | 2.36 | 2.65 | 2.92 | 3.43 | 2.84 | 2.35 | 1.88 | 2.87 |
| | 7 | | 343 | 2.23 | | | | | | | |
| | 8 | | 347 | 3.12 | | | | | | | |
| | 9 | | 340 | 2.41 | | | | | | | |
| | 10 | | 352 | 2.45 | | | | | | | |

10:10 10:15 10:20 10:35 10:50 11:05
Administered 10 ul 0.9% saline solution (vehicle)
IT—Nornicotine Perchlorate & Morphine
   Dose 10 ug nornicotine &+0.5 ug morphine
     10:45 10:50 10:55 11:10 11:25 11:40

| Inject Time | Rat | Treatmt. | Wt. | Baseline | Baseline | 5 min. | 10 min. | 15 min. | 30 min. | 45 min. | 60 min. |
|---|---|---|---|---|---|---|---|---|---|---|---|
| 10:40 | 1 | R + M | 402 | 2.28 | 2.10 | 2.08 | 3.49 | 2.36 | 2.26 | 1.84 | 2.71 |
| 10:40 | 2 | R + M | 334 | 2.25 | 2.89 | 2.88 | 4.78 | 3.05 | 2.03 | 2.21 | 2.68 |
| 10:40 | 3 | R + M | 356 | 2.58 | 2.36 | 3.12 | 5.60 | 2.84 | 3.37 | 1.90 | 3.16 |
| 10:45 | 4 | R + M | 353 | 2.13 | 2.79 | 6.46 | 9.40 | 5.15 | 2.42 | 2.25 | 3.08 |
| | 5 | S + M | — | loose - | did not | use | — | | | | |
| | 6 | S + M | | | | | | | | | |
| | 7 | S + M | | | | | | | | | |
| | 8 | S + M | | | | | | | | | |
| | 9 | S + M | | | | | | | | | |
| | 10 | | | | | | | | | | |

Injection vol.=>5 ul of each drug
   Nornicotine: 10 ug/5 ul=>1 mg in 0.5 ml saline
   Morphine: 0.5 ug/5 ul=>1 mg in 10 ml saline
S—0.0011 g
R—0.0010 g
Mor—0.0010 g
Note: inject rats singly then test=>not enough time to inject
   all 4 then get the 5 min. point.
IT—Nornicotine Perchlorate (10 ug) & Morphine (0.5 mg)

| Inject Time | Rat | Dose | Wt. | Baseline | Baseline | 5 min. | 10 min. | 15 min. | 30 min. | 45 min. | 60 min. |
|---|---|---|---|---|---|---|---|---|---|---|---|
| 12:05 | 6 | S | 389 | 2.58 | 1.99 | 3.99 | 9.17 | 10 | 9.25 | 10 | 9.14 |
| 12:21 | 7 | S | 368 | 2.59 | 2.65 | 2.75 | 2.74 | 3.46 | 4.20 | 3.68 | 2.93 |
| 12:38 | 8 | S | 369 | 3.11 | 3.80 | 4.10 | 7.76 | 10 | 8.12 | 7.26 | 8.71 |
| 12:55 | 9 | S | 356 | 1.93 | 2.09 | 2.29 | 3.75 | 10 | 7.44 | 5.96 | 7.93 |
| 1:13 | 10 | S | 356 | 2.77 | 3.65 | 2.85 | 4.93 | 4.57 | 3.56 | 4.55 | 3.00 |

*Do one injection, then follow rat for 15 min. before starting the next one=>more accurate capture of 5, 10, 15 min. time points.

$$S\text{-nornicotine} = 10 \text{ ug}/5 \text{ ul} = > 1 \text{ mg in } 0.5 \text{ ml saline}$$
$$= 0.0011 \text{ g}$$

Rat #7—consistent with previous data=>no response from
   baseline.

| | ST20 9:15 | | | | | |
|---|---|---|---|---|---|---|
| Rat | 90 min. | 120 min. | 180 min. | 21 hr. | 24 hr. | 26 hr. |
| 6 | 7.45 | 5.37 | 4.77 | 10 | 10 | 10 |
| 7 | | | | | | |

| | -continued | | | | | |
|---|---|---|---|---|---|---|
| | ST20 9:15 | | | | | |
| Rat | 90 min. | 120 min. | 180 min. | 21 hr. | 24 hr. | 26 hr. |
| 8 | 8.21 | 9.01 | 10.00 | 5.11 | 5.26 | 3.25 3.20 |
| 9 | 6.47 | 8.08 | 5.34 | 3.67 | 4.29 | 2.57 2.07 |
| 10 | | | | | | |

Rat #6 (24 hrs.)—doesn't flick tail when pinched.

What is claimed is:

1. A codrug of the following formula:

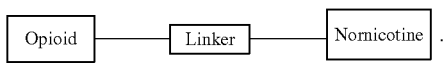

2. The codrug of claim 1, wherein the linker is selected from the group consisting of the following formulae:

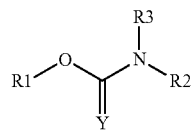

wherein Y is O or S; R1 is an opioid moiety; and R2-N-R3 is a nornicotine moiety and

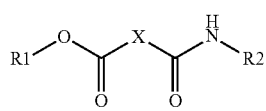

wherein X is nothing, O, S, NH, NR4 (where R4=alkyl), $(CH_2)_x$ (where x=1-20, and alkyl is linear or branched), and wherein R1-O is an opioid moiety and R2-N-R3 is a nornicotine moiety.

3. The codrug of claim 2, wherein the opioid is selected from the group consisting of dihydroetorphine, butorphanol, pentazocine, morphine, phenazocine, hydromorphone, codeine, oxymorphone, 3-acetylmorphine, methadone, propoxyphene, oxycodone, tramadol, hydrocodone, buprenorphine, levorphanol, dihydrocodeine, L-acetylmethadol, ethylmorphine, nalbuphine, etorphine, buprenorphine, normethadone, dihydromorphine, noroxycodone, normorphine, norlevorphanol, and pharmaceutically acceptable salts, metabolites, enantiomers, diastereiomers and isomers thereof.

4. The codrug of claim 1, wherein the nornicotine is selected from the group consisting of S-nornicotine, R-nornicotine, and racemic nornicotine, and pharmaceutically acceptable salts and metabolites thereof.

5. The codrug of claim 1 having the formula Ia:

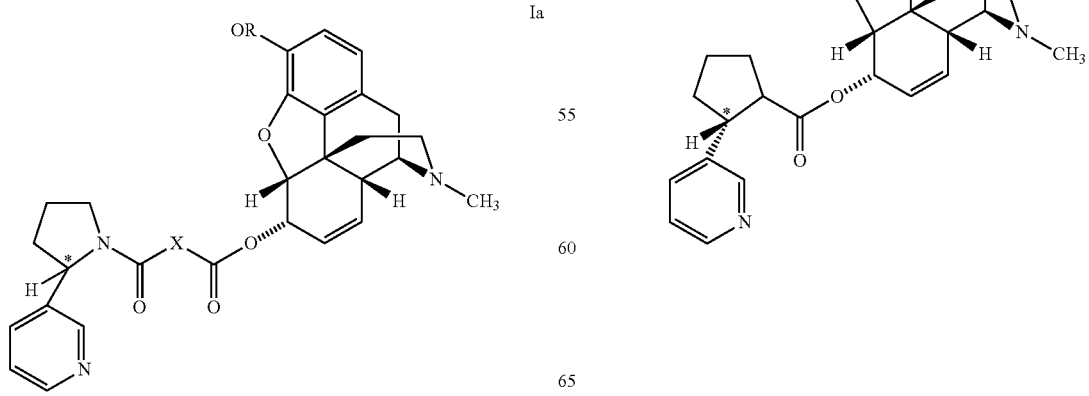

wherein R is H or $CH_3$, or R1-CO— (where R1=alkyl); X a bond, O, S, NH, NR2 (where R2 is alkyl), $(CH_2)_x$ (where x=1-20, and alkyl is either linear or branched); and * represents a racemic nornicotine, S-nornicotine, or R-nornicotine moiety; and stereoisomers thereof.

6. The codrug of claim 1 having the formula Ib:

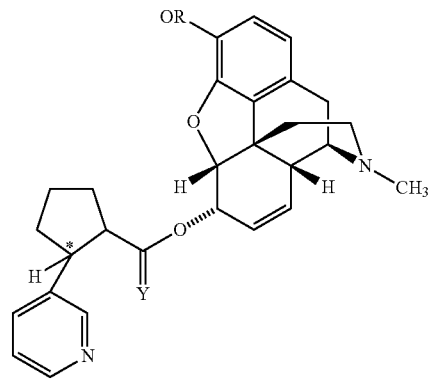

wherein Y is O, S; R is H or $CH_3$ or R1-CO— (where R1=alkyl); and * represents a racemic nornicotine, S-nornicotine, or R-nornicotine moiety; and stereoisomers thereof.

7. The codrug of claim 1 having the formula II:

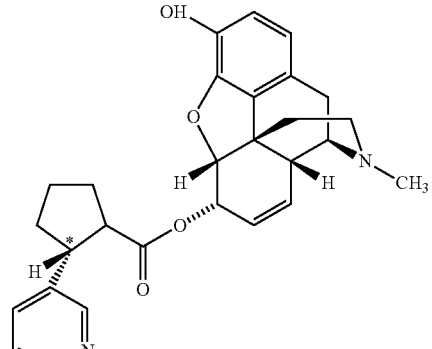

and stereoisomers thereof, wherein the nornicotine is S-nornicotine.

8. The codrug of claim 1 having the formula III:

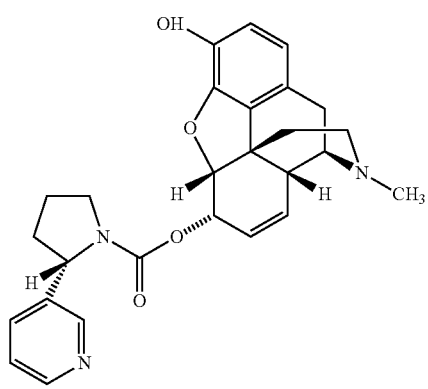

and stereoisomers thereof, wherein the nornicotine is R-nornicotine.

9. A codeine-S-nornicotine codrug comprising the formula:

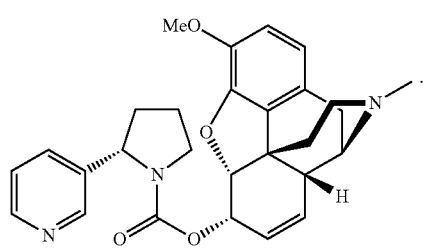

10. A 3-acetylmorphine-S-nornicotine codrug comprising the formula:

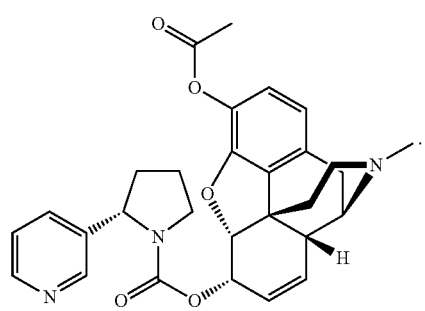

11. The codrug of claim 1, wherein the opioid moiety is morphine, and the nornicotine moiety is S-nornicotine, and wherein the linker is a carbamate.

12. The The codrug of claim 1, wherein the opioid moiety is 3-acetylmorphine, and the nornicotine moiety is S-nornicotine, and wherein the linker is a carbamate.

13. The codrug of claim 1, wherein the opioid moiety is codeine, and the nornicotine moiety is S-nornicotine, and wherein the linker is a carbamate.

14. The codrug of claim 1, wherein the opioid moiety is oxycodone, and the nornicotine moiety is S-nornicotine, and wherein the linker is a carbamate.

15. The codrug of claim 1, wherein the opioid moiety is oxymorphone, and the nornicotine moiety is S-nornicotine, and wherein the linker is a carbamate.

16. The codrug of claim 1, wherein the opioid moiety is hydromorphone, and the nornicotine moiety is S-nornicotine, and wherein the linker is a carbamate.

17. The codrug of claim 1, wherein the opioid moiety is butorphanol, and the nornicotine moiety is S-nornicotine, and wherein the linker is a carbamate.

18. The codrug of claim 1, wherein the opioid moiety is bupernorphine, and the nornicotine moiety is S-nornicotine, and wherein the linker is a carbamate.

19. The codrug of claim 1, wherein the opioid moiety is tramadol, and the nornicotine moiety is S-nornicotine, and wherein the linker is a carbamate.

20. The codrug of claim 1, wherein the opioid moiety is levorphanol, and the nornicotine moiety is S-nornicotine, and wherein the linker is a carbamate.

21. A pharmaceutical composition comprising an analgesically effective amount of a compound selected from the group consisting of:

a compound of the formula Ia:

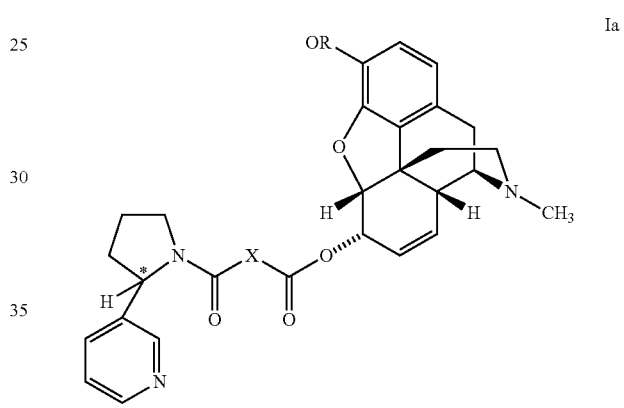

wherein R is H or $CH_3$, R1-CO— (where R1=alkyl); X is a bond, S, O, NH, NR2 (where R2=alkyl); and * represents a racemic nornicotine, S-nornicotine, or R-nornicotine moiety;

a compound of the formula Ib:

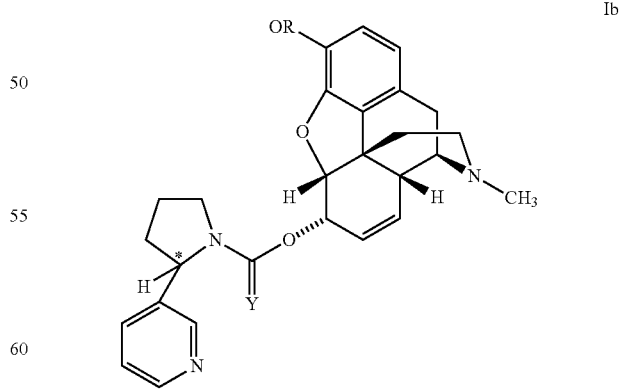

wherein Y is O, S; R is H or $CH_3$ or R1-CO— (where R1=alkyl); and * represents a racemic nornicotine, S-nornicotine, or R-nornicotine moiety; and analogs and stereoisomers thereof, a compound of the formula II:

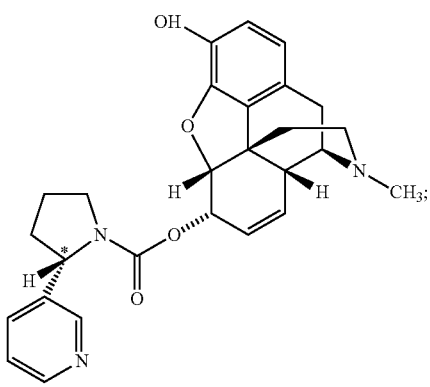

and a compound of the formula III:

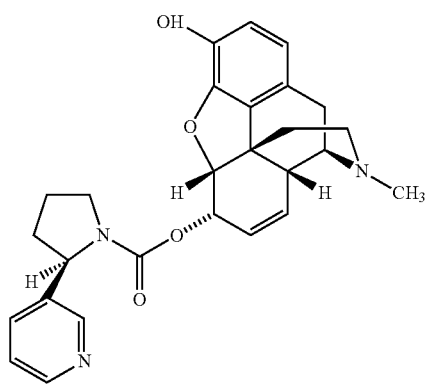

and at least one pharmaceutically acceptable excipient.

22. A pharmaceutical composition comprising the compound of claim 9 and at least one pharmaceutically acceptable excipient.

23. A pharmaceutical composition comprising the compound of claim 10 and at least one pharmaceutically acceptable excipient.

24. The pharmaceutical composition of claim 21, wherein the composition is a formulation suitable for a route of administration selected from the group consisting of oral, sublingual, oral inhalation, nasal inhalation, sublingual, rectal, vaginal, urethral, intravenous, intra-arterial, intradermal, intramuscular, subcutaneous, transdermal, mucosal and buccal.

25. A pharmaceutical composition comprising the codrug of claim 11, wherein the release of the codrug is substantially controlled over an extended period of time of about 4 hours to about 96 hours.

26. The pharmaceutical composition of claim 25, wherein the release of the codrug is substantially controlled for about 6-12 hours.

27. The pharmaceutical composition of claim 25, wherein the release of the codrug is substantially controlled for about 12-24 hours.

28. A method of synthesis of a codrug comprising a linker, an opioid and a nornicotine, said method comprising:
    a) covalently bonding a first attachment point of the linker to the opioid;
    b) covalently bonding a second attachment point of the linker to the nornicotine; and
    c) recovering the codrug,
wherein the nornicotine is selected from the group consisting of S-nornicotine, R-nornicotine, and racemic nornicotine.

29. The method of claim 28, wherein the method further comprises:
    a) reacting para-nitrophenyl chloroformate with an opiate (opioid) (R1) containing a hydroxy group in the presence of triethyl amine and dry chloroform;
    b) cooling the solution;
    c) recovering the resulting 6-O-para-nitrophenoxycarbonate ester of an opiate drug;
    d) reacting the 6-O-para-nitrophenoxycarbonate ester of an opiate drug with a nornicotine drug (R2); and
    e) recovering the nornicotine-opioid codrug.

30. The method of claim 28, wherein step b) is reacted in the presence of dry THF and triethyl amine.

31. The method of claim 28, wherein step b) occurs under cooled conditions and in a nitrogen atmosphere.

32. A method of treatment comprising:
    joining an opioid together with a nornicotine using a linker to form a cleavable codrug; and
    administering an analgesically effective amount of the codrug to a human patient in need thereof,
wherein the nornicotine is selected from the group consisting of S-nornicotine, R-nornicotine, and racemic nornicotine.

33. The method of claim 32, wherein the codrug substantially remains intact until it reaches the site of action of at least the opioid or the nornicotine.

34. The method of claim 32, wherein the codrug is more lipophilic than the opioid molecule.

* * * * *